United States Patent
Shih et al.

(10) Patent No.: US 6,762,186 B2
(45) Date of Patent: Jul. 13, 2004

(54) SUBSTITUTED IMIDAZOLES AS DUAL HISTAMINE H1 AND H3 AGONISTS OR ANTAGONISTS

(75) Inventors: Neng-Yang Shih, North Caldwell, NJ (US); Robert G. Aslanian, Rockaway, NJ (US); Daniel M. Solomon, Edison, NJ (US); Stuart B. Rosenblum, West Orange, NJ (US); Mwangi Wa Mutahi, Edison, NJ (US); Tom G. Wing, Cedar Grove, NJ (US); Kevin D. McCormick, Edison, NJ (US); John J. Piwinski, Clinton Township, NJ (US); Ronald Wolin, San Diego, CA (US)

(73) Assignee: Schering Corporation, Kenilworth, NJ (US)

( * ) Notice: Subject to any disclaimer, the term of this patent is extended or adjusted under 35 U.S.C. 154(b) by 31 days.

(21) Appl. No.: 09/955,383

(22) Filed: Sep. 18, 2001

(65) Prior Publication Data

US 2002/0082278 A1 Jun. 27, 2002

Related U.S. Application Data

(60) Provisional application No. 60/234,039, filed on Sep. 20, 2000.

(51) Int. Cl.$^7$ .................. C07D 211/68; C07D 401/00; A61K 31/445; A61K 31/495
(52) U.S. Cl. ................ 514/253.09; 546/194; 544/364; 514/318
(58) Field of Search ................ 546/194; 514/318, 514/253.09; 544/364

(56) References Cited

U.S. PATENT DOCUMENTS

| | | | |
|---|---|---|---|
| 4,767,778 A | 8/1988 | Arrang et al. | 514/397 |
| 5,352,707 A | 10/1994 | Pompni et al. | 514/151 |
| 5,869,479 A | 2/1999 | Kreutner et al. | 514/212 |

FOREIGN PATENT DOCUMENTS

| | | |
|---|---|---|
| EP | 0448 765 B1 | 3/1990 |
| EP | 0 420 396 B1 | 7/1990 |
| WO | WO 93/01812 | 2/1993 |
| WO | WO 93/12093 | 6/1993 |
| WO | WO 95/14007 | 5/1995 |
| WO | WO 96/29315 | 9/1996 |
| WO | WO 98/58646 | 12/1998 |

OTHER PUBLICATIONS

Howson, Bioorganic & Medicinal Chemistry Letters, Two Novel, Potent and Selective Histamine H3 Receptor Agonists, vol. 2, pp. 77–78, 1992.

Stark, J. Med. Chem. , Novel Carbamates as Potent Histamine H3 Receptor Antagonists with High in Vitro and Oral In Vivo Activity, 39, pp. 1157–1163.
Sasse, Bioorganic & Medicinal Chemistry , (Partial) Agonist/Antagonist Properties of Novel Diarylalkyl, vol. 8 (2000) pp. 1139–1149.
Bagley, J. Med. Chem. 1991, New 1–(Heterocyclylalkyl)–4–(Propionanilido)–4–Piperidinyl, 34, pp 827–941.
Huls, Bioorganic & Medicinal Chemistry Letters, Diphenylmethyl Ethers: Synthesis and Histamine, vol. 6, No. 16, pp. 2013–2018, 1996.
Buschauer, J. Med. Chem. 1989, Synthesis and in Vitro Pharmacology of Arpromidine, 32, pp 1963–1970, 1989.
Schulze, Arch. Pharm. (Weinhelm), Synthese und kombinierte H1/H2–antagonistische, vol. 327, pp. 455–462, 1994.
Schulze, European Journal of Pharmaceutical Sciences, Combined histamine H1/H2 receptor antagonists, vol. 6, pp. 177–186, 1998.
van der Goot, Eur J. Med. Chem. , Isothiourea analogues of histamine as potent agonists, vol. 27, pp. 511–517, 1992.
Walczynski, II Farmaco, Non–imidazole histamine H3 ligands, Vo. 54, pp. 684–694, 1999.
Brown, Br. J. Pharmac. , Pharmacological studies with SK & F 93944, vol. 87, pp. 569–578, 1986.
West, Molecular Pharmacology, Identificatin of Two H3–Histamine Receptor Subtypes, vol. 38, pp. 610–613, 1990.
Clapham, Brit. J. Pharm. Suppl. , Ability of the Selective Histamine H3 Receptor Antagonist, vol. 110, pp. Abs. 65P, 00/00, 1993.
Yokoyama, European Journal of Pharmacology, Effect of Thioperamide, vol. 234, pp 129–133, 1993.
Schlicker, Br. J. Pharmacol., Novel Histamine H3 Receptor Antagonists, vol. 112, pp. 1043–1048, 1994.
Leurs, Progre. Drug. Res. , The Histamine H3–Receptor, vol. 39, pp. 127–165, 00/00, 1992.
Lipp, Histamine Receptor, Pharmacochemistry of H3–Receptors, pp. 57–72, 00/00, 1992.
Stark, European Journal of Pharmaceutical Sciences, New potent Histamine H3–Receptor vol. 3, pp. 95–104, 1995.

*Primary Examiner*—Richard L. Raymond
*Assistant Examiner*—Hong Liu
(74) *Attorney, Agent, or Firm*—Palaiyur S. Kalyanaraman

(57) ABSTRACT

The present invention discloses novel substituted imidazole compounds which have $H_3$ receptor antagonist or dual histamine-$H_1$ and $H_3$ receptor antagonist activity as well as methods for preparing such compounds. In another embodiment, the invention discloses pharmaceutical compositions comprising such imidazoles as well as methods of using them to treat allergy, nasal congestion, inflammatory and CNS-related diseases and others.

7 Claims, No Drawings

SUBSTITUTED IMIDAZOLES AS DUAL HISTAMINE H1 AND H3 AGONISTS OR ANTAGONISTS

The invention disclosed in this application claims priority from provisional application Ser. No. 60/234,039 filed Sep. 20, 2000, and is related to that in pending provisional applications, Ser. No. 60/234,040, Ser. No. 60/234,038, and Ser. No. 60/234,053, all filed on Sep. 20, 2000.

FIELD OF THE INVENTION

The present invention relates to novel substituted imidazole compounds having valuable pharmacological properties, especially against inflammatory diseases and allergic conditions. Compounds of this invention are antagonists of the histamine receptors. Some are antagonists of the histamine-$H_3$ receptors. Some are antagonists of both the $H_1$ and $H_3$ receptors, in other words dual $H_1$ and $H_3$ receptor antagonists.

BACKGROUND OF THE INVENTION

The histamine receptors, $H_1$, $H_2$ and $H_3$ are well-identified forms. The $H_1$ receptors are those that mediate the response antagonized by conventional antihistamines. $H_1$ receptors are present, for example, in the ileum, the skin, and the bronchial smooth muscle of humans and other mammals. A well-known antagonist of $H_1$ receptors is loratadine, commercially available under the tradename CLARITIN® from Schering-Plough Corporation, Madison, N.J. Through $H_2$ receptor-mediated responses, histamine stimulates gastric acid secretion in mammals and the chronotropic effect in isolated mammalian atria.

$H_3$ receptor sites are found on sympathetic nerves, where they modulate sympathetic neurotransmission and attenuate a variety of end organ responses under control of the sympathetic nervous system. Specifically, $H_3$ receptor activation by histamine attenuates nonepinephrine outflow to resistance and capacitance vessels, causing vasodilatation.

U.S. Pat. No. 4,767,778 (Arrang et al.) discloses certain imidazoles that behave as agonists of the $H_3$ receptors in rat brain. European Patent Application No. 0 420 396 A2 (Smith Kline & French Laboratories Limited) and Howson et al. (*Bioorg. & Med. Chem. Letters*, (1992), Vol. 2 No. 1, pp. 77–78) describe imidazole derivatives having an amidine group as $H_3$ agonists. Van der Groot et al. (*Eur. J. Med. Chem.* (1992) Vol. 27, pp. 511–517) describe isothiourea analogs of histamine as potent agonists or antagonists of the histamine-$H_3$ receptor, and these isothiourea analogs of histamine overlap in part with those of the two references cited above. Clapham et al. ["Ability of Histamine-$H_3$ Receptor Antagonists to Improve Cognition and to Increase Acetylcholine Release in vivo in the Rat", *British Assn. for Psychopharmacology*, Jul. 25–28 (1993), reported in *J. Psychopharmacol.* (Abstr. Book), A 17] describe the ability of histamine-$H_3$ receptor antagonists to improve cognition and to increase release of acetylcholine in vivo in the rat. Clapham et al. ["Ability of the selective Histamine-$H_3$ Receptor Antagonist Thioperamide to improve Short-term Memory and Reversal Learning in the Rat", *Brit. J. Pharm. Suppl.*[1993, 110, Abstract 65P] present results showing that thioperamide can improve short-term memory and reversal learning in the rat and implicate the involvement of $H_3$ receptors in the modulation of cognitive function. Yokoyama et al. ["Effect of Thioperamide, a Histamine-$H_3$ Receptor Antagonist, on Electrically Induced Convulsions in Mice", *Eur. J. Pharmacol.* (1993), Vol. 234, pp.129–133] report how thioperamide decreased the duration of each phase of convulsion and raised the electroconvulsive threshold, and go on to suggest that these and other findings support the hypothesis that the central histaminergic system is involved in the inhibition of seizures. International Patent Publication No. WO 9301812-A1 (SmithKline Beecham PLC) describes the use of S-[3-(4(5)-imidazolyl)propyl] isothiourea as a histamine-$H_3$ antagonist, especially for treating cognitive disorders, e.g. Alzheimer's disease and age-related memory impairment. Schlicker et al. ["Novel Histamine-$H_3$ Receptor Antagonists: Affinities in an $H_3$ Receptor Binding Assay and Potencies in Two Functional $H_3$ Receptor Models", *British J. Pharmacol.*, (1994), Vol. 112, 1043–1048] describe a number of imidazolylalkyl compounds wherein the imidazolylalkyl group is bonded to a guanidine group, an ester group, an amide group, a thioamide group and a urea group, and compared these to thioperamide. Leurs et al. ["The Histamine-$H_3$-receptor: A Target for Developing New Drugs", *Progr. Drug Res.* (1992), Vol. 39, pp.127–165] and Lipp et al. ["Pharmacochemistry of $H_3$-receptors" in *The Histamine Receptor*, eds.: Schwartz and Haas, Wiley-Liss, New York (1992), pp. 57–72] review a variety of synthetic $H_3$ receptor antagonists, and Lipp et al. (ibid.) have proposed the necessary structural requirements for an $H_3$ receptor antagonist.

WO 95/14007 claims $H_3$ receptor antagonists of the formula

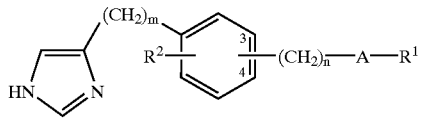

wherein A, m, n, $R^1$ and $R^2$ are defined therein. The compounds are disclosed as being useful for treating various disorders, in particular such caused by allergy-induced responses.

WO 93/12093 discloses imidazolylmethyl piperazines and diazepines as $H_3$ antagonists. U.S. patent application, Ser. No. 08/965,754, filed Nov. 7, 1997, discloses imidazolylalkyl substituted heterocyclic ring compounds as $H_3$ receptor antagonists. U.S. patent application, Ser. No. 08/966,344, filed Nov. 7, 1997, discloses phenylalkylimidazoles as $H_3$ receptor antagonists.

WO 96/29315 (PCT/FR96/00432) discloses certain N-imidazolylalkyl compounds containing phenyl moieties attached.

Also disclosing $H_3$ receptor antagonists are: H. Stark et al, *Eur. J. of Pharmaceutical Sciences* (1995) 3, 95–104; H. Stark et at, *J. Med. Chem.*, (1996) 39, 1157–1163; H. Stark et al, *Arch. Pharm. Pharm. Med. Chem.*, (1998) 331, 211–218; and A. Sasse et at, *Bioorganic & Medicinal Chem.*, (2000) 8, 1139–1149.

Reference is also made to J. R. Bagley et al. *Journal of Medicinal Chemistry*, (1991), Vol. 34, 827–841, which discloses, among others, N-(imidazolylalkyl) substituted cyclic amine compounds useful as analgesics such as the amine compound with the formula:

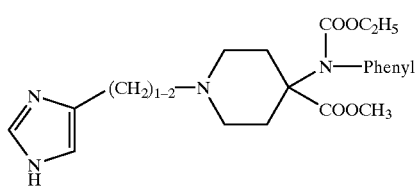

Pending U.S. patent application, Ser. No. 09/173,642, filed Oct. 16, 1998 (R. Wolin et al.), discloses N-(imidazolylalkyl) substituted cyclic amine compounds having $H_3$ antagonist activity.

A. Huls et al., *Bioorg. & Med. Chem. Letters*, 6 (1996), 2013–2018 disclose imidazole compounds containing diphenyl ether moieties as $H_3$ receptor antagonists. The compounds are additionally disclosed to have $H_1$ receptor antagonist activity. An example compound from that publication is:

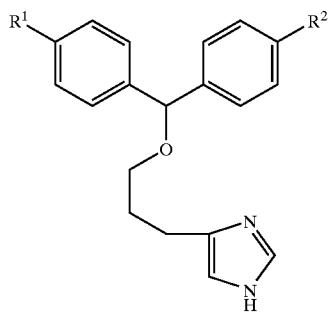

where $R^1$ and $R^2$ are defined therein.

A. Buschauer, *J. Med. Chem.*, 32 (1989), 1963–1970 disclose, among others, $H_2$ receptor antagonists of the type:

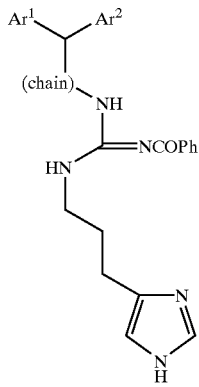

where $Ar^1$ and $Ar^2$ may be phenyl and/or pyridyl. EPO 448,765 A1 (published Mar. 30, 1990) discloses neuropeptide-Y antagonist imidazoles of the type:

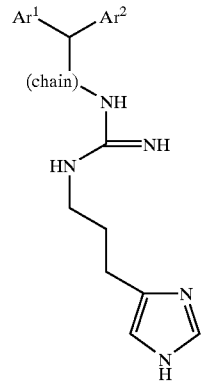

where $Ar^1$ and $Ar^2$ may be phenyl and/or pyridyl.
WO 98-58646 (assigned to Novo Nordisk A/S) discloses somatostatin SSTR4 receptor antagonist compounds of the type:

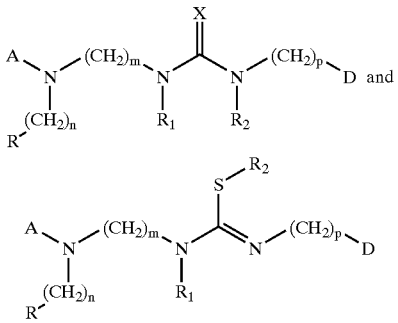

wherein m is 2–6; n is 1–3; p is 1–6; $R_1$ and $R_2$ are independently H or C1–C6 alkyl optionally substituted with halogen, amino, hydroxy, alkoxy or aryl; X is S, O, NH, NCOPh or N(CN); A is aryl optionally substituted with halogen, amino, hydroxy, nitro, C1–6 alkyl, C1–6 alkoxy, or aryl; and B and D are independently aryl optionally substituted with halogen, amino, hydroxy, C1–6 alkyl, C1–6 alkoxy, or aryl.

Compounds have been reported in the literature as having activity against both $H_1$ and $H_2$ receptors, i.e. dual antagonists against $H_1$ and $H_2$ receptors. Thus, for example, F. Schulze et al., *European J. of Pharmaceutical Sciences*, 6 (1998), 177–186 report combined $H_1/H_2$ receptor antagonists. Other references in this category include F. Schulze et al., *Arch. Pharm. (Weinheim)*, 327 (1994), 455–462; C. Wolf et al., *Arch. Pharm. Pharm. Med. Chem.*, 329 (1996), 87–94; and C. Wolf et al., *European J. of Pharmaceutical Sciences*, 6 (1998), 177–186. Non-imidazole histamine $H_3$ ligands, particularly substituted benzothiazole derivatives as $H_3$ antagonists and $H_1$ blocking activities have been reported by K. Walczynski et al, *Il Farmaco*, 54 (1999), 684–694.

It would be useful to have compounds which are therapeutically effective as antagonists of both the $H_1$ and $H_3$ histamine receptors. The only such reported activity has been through a combination of two different chemical entities, one showing activity against H. receptors and the other showing activity against $H_3$ receptors. Thus, for example, U.S. Pat. No. 5,869,479 (issued Feb. 9, 1999 to Schering Corporation) discloses the combination of a histamine-$H_1$ receptor antagonist and a histamine-$H_3$ receptor antagonist for the treatment of allergy-induced airway responses.

Pending provisional patent application, Ser. No.60/234, 040, filed Sep. 20, 2000, discloses novel imidazole compounds having $H_3$ as well as dual $H_1$ and $H_3$ antagonist activity. The compounds disclosed therein have general formula in which an imidazole is linked to two cyclic moieties via intermediary moiety or moieties which intermediary moiety or moieties are acyclic.

Pending provisional patent application, Ser. No. 60/234, 038, filed Sep. 20, 2000, discloses novel imidazole compounds having $H_3$ as well as dual $H_1$ and $H_3$ antagonist activity. The compounds disclosed therein have general formula in which an imidazole is linked to a tricyclic moiety via intermediary moiety or moieties which intermediary moiety or moieties are all acyclic moieties.

Pending provisional patent application, Ser. No. 60/234, 053, filed Sep. 20, 2000, discloses novel imidazole compounds having $H_3$ as well as dual $H_1$ and $H_3$ antagonist activity. The compounds disclosed therein have general formula in which an imidazole is linked to a tricyclic moiety via intermediary moiety or moieties at least one of which intermediary moiety or moieties is a cyclic moiety.

It would be a welcome contribution to the art to have novel substituted imidazole compounds.

It would be useful to have the same chemical entity showing dual activity against both $H_1$ and $H_3$ receptors.

It would be useful to have novel substituted imidazoles showing activity against both $H_1$ and $H_3$ receptors.

This invention provides just such a contribution by providing novel substituted imidazole compounds having dual $H_1$ and $H_3$ antagonist activity.

SUMMARY OF THE INVENTION

In one embodiment, this invention provides novel substituted imidazole compounds having $H_3$ antagonist activity as well as dual $H_1$ and $H_3$ antagonist activity. The inventive compounds are substituted imidazoles wherein the imidazole is linked to two cyclic moieties via an intermediary moiety or moieties at least one of said intermediary moiety or moieties is a cyclic moiety having the general structure shown in Formula I:

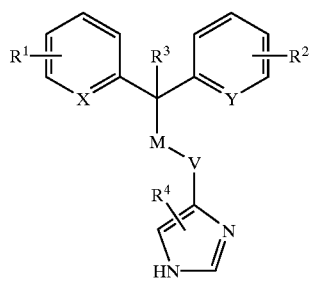

Formula I

M is a moiety having a general structure shown in Formula II or III:

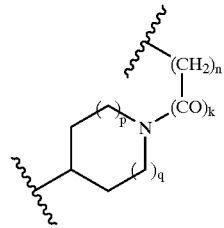

II

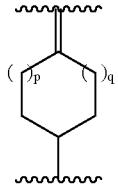

III where k=0 or 1, n 0–5, and p=q=0, 1 or 2 with the proviso that when M is Formula III, $R^3$ is absent;

V is a moiety selected from the group consisting of $C_1$–$C_8$ alkyl; —$(CH_2)_x$—A—$(CH_2)_y$—; and —$(CH_2)_c$—A—$(CH_2)_m$—C(O)—N($R^7$)—$(CH_2)_d$—, where A is —O—, —S(O)$_r$—, and —N$R^7$—; m=0, 1, 2 or 3; x is a whole number in the range 2–8; y is a whole number in the range 1–5; c is a whole number in the range 2–4; and r=0, 1 or 2; d is a number in the range 0–5;

X and Y are independently selected from the group consisting of N, CH, and N(O);

Z is selected from the group consisting of N, CH and N(O);

$R^1$ and $R^2$ may each number 1–4 and are independently selected from the group consisting of hydrogen, lower alkyl, lower alkoxy, halogen, polyhalolower alkyl, polyhalolower alkoxy, —OH, CN, $NO_2$, or $COOR^8$;

$R^3$ is selected from hydrogen, lower alkyl, lower alkoxy, hydroxyl, with the proviso that when n and k are both 0, then $R^3$ is not —OH or alkoxy;

$R^4$ is selected from the group consisting of hydrogen, lower alkyl, polyhalolower alkyl or —OH; and $R^7$ and $R^8$ are independently selected from hydrogen, lower alkyl, substituted or unsubstituted phenyl; and substituted or unsubstituted benzyl.

When used herein, the following terms have the given meanings:

lower alkyl (including the alkyl portions of lower alkoxy)—represents a straight or branched, saturated hydrocarbon chain having from 1 to 6 carbon atoms, preferably from 1 to 4;

aryl—represents a carbocyclic group having from 6 to 14 carbon atoms and having at least one benzenoid ring, with all available substitutable aromatic carbon atoms being intended as possible points of attachment. Preferred aryl groups include 1-naphthyl, 2-naphthyl and indanyl, and especially phenyl and substituted phenyl;

cycloalkyl—represents a saturated carbocyclic ring having from 3 to 8 carbon atoms, preferably 5 or 6, optionally substituted.

heterocyclic—represents, in addition to the heteroaryl groups defined below, saturated and unsaturated cyclic organic groups having at least one O, S and/or N atom interrupting a carbocyclic ring structure that consists of one ring or two fused rings, wherein each ring is 5-, 6- or 7-membered and may or may not have double bonds that lack delocalized pi electrons, which ring structure has from 2 to 8, preferably from 3 to 6 carbon atoms, e.g., 2-, 3- or 4-piperidinyl, 2- or 3-piperazinyl, 2- or 3-morpholinyl, or 2- or 3-thiomorpholinyl;

halogen—represents fluorine, chlorine, bromine and iodine;

heteroaryl—represents a cyclic organic group having at least one O, S and/or N atom interrupting a carbocyclic ring structure and having a sufficient number of delocalized pi electrons to provide aromatic character, with the aromatic heterocyclic group having from 2 to 14, preferably 4 or 5 carbon atoms, e.g., 2-, 3- or 4-pyridyl, 2- or 3-furyl, 2- or 3-thienyl, 2-, 4- or 5-thiazolyl, 2- or 4-imidazolyl, 2-, 4- or 5-pyrimidinyl, 2-pyrazinyl, or 3- or 4-pyridazinyl, etc. Preferred heteroaryl groups are 2-, 3- and 4-pyridyl; such heteroaryl groups may also be optionally substituted.

The term "substituted", unless otherwise defined, refers to chemically suitable substitution with moieties such as, for example, alkyl, alkoxy, —$CF_3$, halogen or aryl.

Furthermore, the term "alkyl", when chemically suitable, also includes alkylene and related moieties. Thus, for example, the above-described definitions for G and V, could also include moieties such as, for example, ethylene, butylene, —$CH_2$—$CH(CH_3)$—, —$CH_2$—$C(=CH_2)$—, and the like.

Also included in the invention are tautomers, enantiomers and other optical isomers of compounds of Formula I, as well as pharmaceutically acceptable salts and solvates thereof.

A further feature of the invention is pharmaceutical compositions containing as active ingredient a compound of Formula I (or its salt, solvate or isomers) together with a pharmaceutically acceptable carrier or excipient.

The invention also provides methods for preparing compounds of Formula I, as well as methods for treating diseases such as, for example, inflammation, allergy, diseases of the GI-tract, cardiovascular disease, or disturbances of the central nervous system as well as allergy-induced airway (e.g., upper airway) responses, congestion and obesity. The methods for treating comprise administering to a mammalian patient (including humans and animals) suffering from said disease or diseases a therapeutically effective amount of a compound of Formula I, or pharmaceutical compositions comprising a compound of Formula I.

DETAILED DESCRIPTION OF THE INVENTION

In one embodiment, the present invention provides novel imidazole compounds of Formula I above where the various symbols are also defined. Representative compounds of the invention which exhibit good $H_3$ antagonist activity are listed below:

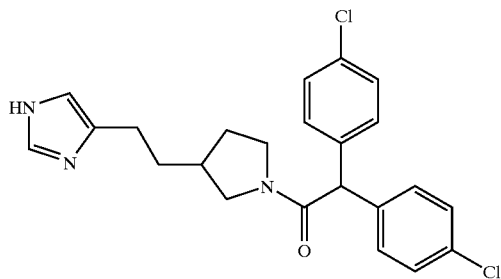

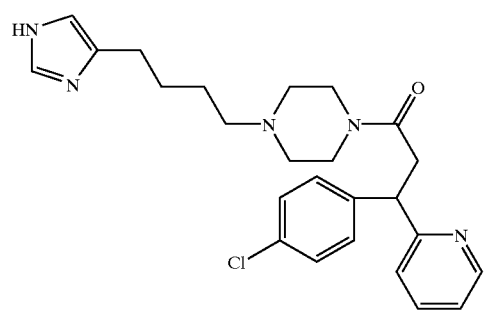

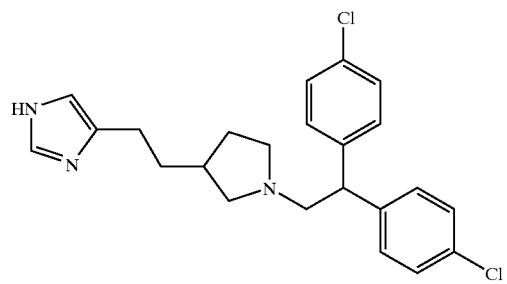

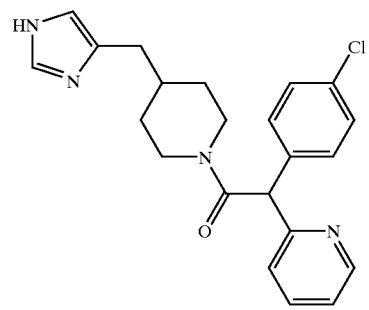

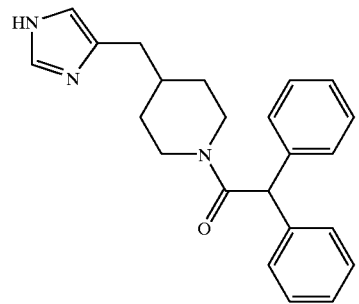

Some examples of compounds exhibiting both $H_1$ and $H_3$ activity include:

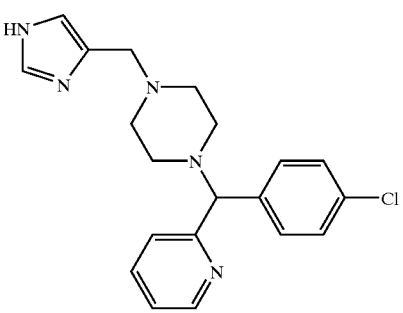

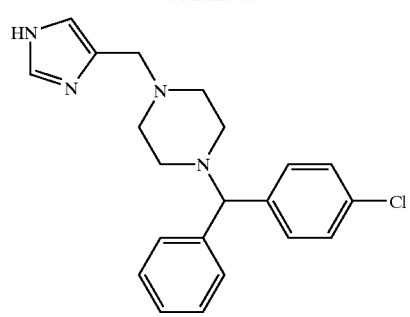
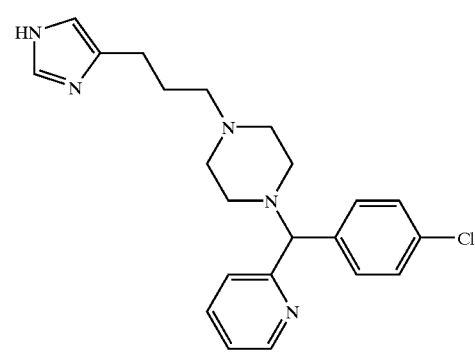
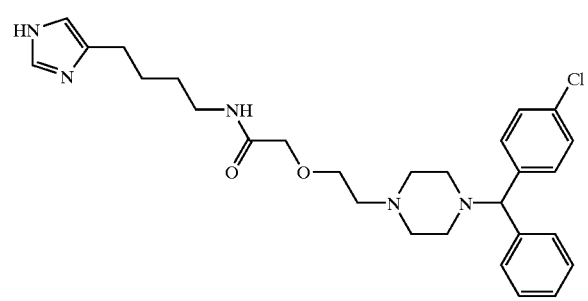
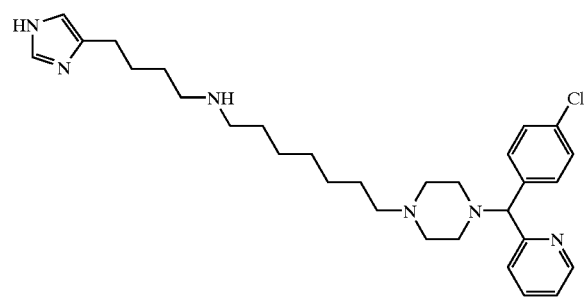
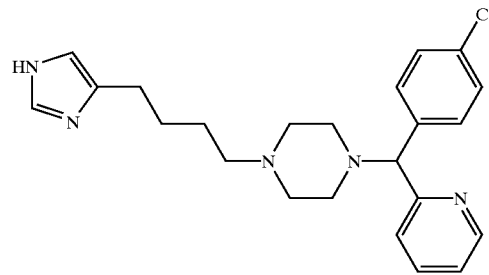
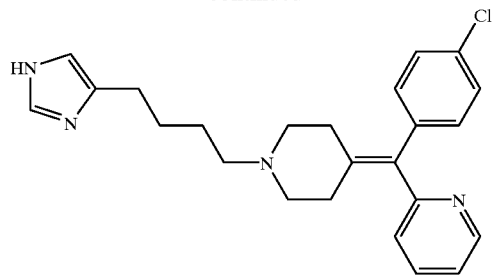
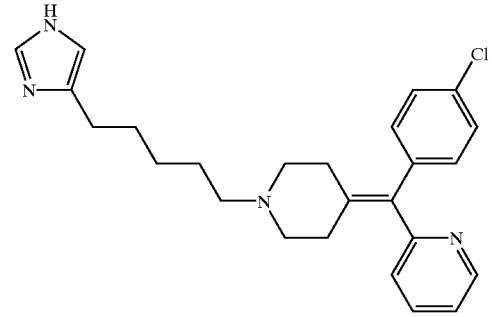
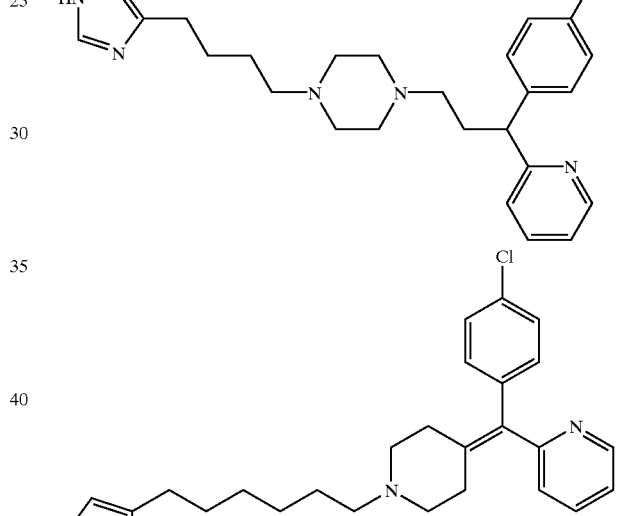
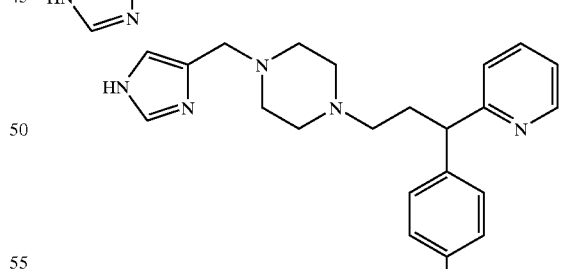
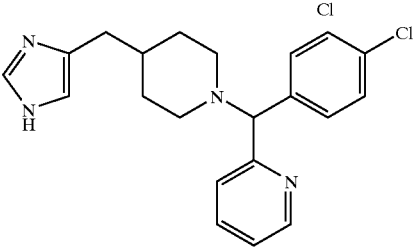

The compounds of the invention are basic and form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their corresponding salt forms somewhat in certain physical properties, such as solubility in polar solvents, but the salts are otherwise equivalent to their corresponding free base forms for purposes of this invention.

Depending upon the substituents on the inventive compounds, one may be able to form salts with bases too. Thus, for example, if there are carboxylic acid substituents in the molecule, salts may be formed with inorganic as well as organic bases such as, for example, NaOH, KOH, $NH_4OH$, tetraalkylammonium hydroxide, and the like.

As stated earlier, the invention includes tautomers, enantiomers and other stereoisomers of the compounds also. Thus, as one skilled in the art knows, certain imidazole compounds may exist in tautomeric forms. Such variations are contemplated to be within the scope of the invention.

Another embodiment of the invention discloses a method of making the substituted imidazoles disclosed above. The compounds may be prepared by several processes well known in the art. In one method, the imidazole part (designated "the left side component" herein for simplicity purposes) and the diaryl part (designated "the right side component" herein for simplicity purposes) may be prepared separately. The left side component and the right side component may contain reactive moieties attached to them, which moieties are suitable to be reacted with each other under appropriate reaction conditions. Thus, for example, the left side component may contain a carboxy or carboxylic acid end, and the right side component may have an amine end. Under appropriate reaction conditions, the two components may be reacted together whereby an imidazole containing a diaryl alkyl moiety linked through an extended amide chain is obtained. Other substituted imidazoles may similarly be prepared.

Isolation of the compound at various stages of the reaction may be achieved by standard techniques such as, for example, filtration, evaporation of solvent and the like. Purification of the product, intermediate and the like, may also be performed by standard techniques such as recrystallization, distillation, sublimation, chromatography, conversion to a suitable derivative which may be recrystallized and converted back to the starting compound, and the like. Such techniques are well known to those skilled in the art.

The compounds thus prepared may be analyzed for their composition and purity as well as characterized by standard analytical techniques such as, for example, elemental analysis, NMR, mass spectroscopy, and IR spectra.

The inventive compounds can readily be evaluated to determine activity at both $H_1$ and $H_3$ receptors by known methods, such as, for example, E. A. Brown et al., *British J. Pharm.*, (1986) Vol. 80, 569. $H_3$ activity may be determined by, for example, the guinea pig brain membrane assay and the guinea pig neuronal ileum contraction assay, both of which are described in U.S. Pat. No. 5,352,707. Another useful assay for $H_3$ activity utilizes rat brain membranes and is described by West et al., ("Identification of Two $H_3$-Histamine Receptor Subtypes", *Molecular Pharmacology*, (1990), Vol. 33, 610–613. Several of the present compounds were found to have high $H_1$ and $H_3$ antagonist activity which is discussed more in the EXAMPLES section below.

In another embodiment, this invention provides pharmaceutical compositions comprising the above-described inventive imidazoles as an active ingredient. The pharmaceutical compositions generally additionally comprise a pharmaceutically acceptable carrier diluent, excipient or carrier (collectively referred to herein as carrier materials). Because of their $H_1$ and $H_3$ antagonist activity, such pharmaceutical compositions possess utility in treating allergy, inflammation, nasal congestion, hypertension, glaucoma, sleeping disorders, states of hyper- and hypomotility of the gastrointestinal tract, hypo- and hyperactivity of the central nervous system, Alzheimers, schizophrenia, migraines, obesity and like diseases.

In yet another embodiment, the present invention discloses methods for preparing pharmaceutical compositions comprising the inventive imidazole compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the controlled release of any one or more of the components or active ingredients to optimize the therapeutic effects, i.e. antihistaminic activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refers to the active ingredients dispersed or solubilized in a hydrophillic semi-solid matrix.

Powders for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d,l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses use of the pharmaceutical compositions disclosed above for treatment of diseases such as, for example, allergy, inflammation, nasal congestion, hypertension, glaucoma, sleeping disorders, states of hyper- and hypo-motility of the gastrointestinal tract, hypo- and hyperactivity of the central nervous system, Alzheimers, schizophrenia, migraines, obesity and the like. The method comprises administering a therapeutically effective amount of the inventive pharmaceutical composition to a mammalian patient having such a disease or diseases and in need of such a treatment.

Those skilled in the art will realize that the term "upper airway" means the upper respiratory system—i.e., the nose, throat, and associated structures.

It will be apparent to those skilled in the art that many modifications, variations and alterations to the present disclosure, both to materials and methods, may be practiced. Such modifications, variations and alterations are intended to be within the spirit and scope of the present invention.

The following EXAMPLES are being provided to further illustrate the present invention. They are for illustrative purposes only; the scope of the invention is not to be considered limited in any way thereby.

EXAMPLES

Unless otherwise stated, the following abbreviations have the stated meanings in the Examples below:
DBU=1,8-diazabicyclo[5.4.0]undec-7-ene
DBN=1,5-diazabicyclo[4.3.0]non-5-ene
EDCl=1-(3-dimethylaminopropyl)-3-ethylcarbodiimide
HOBT=1-hydroxybenzotriazole
DCC=dicyclohexylcarbodiimide
Dibal-H=diisobutylaluminum hydride
LAH=lithium aluminum hydride
NaBH(OAc)$_3$=sodium triacetoxyborohydride
NaBH$_4$=sodium borohydride
NaBH$_3$CN=sodium cyanoborohydride
LDA=lithium diisopropylamide
p-TsOH=p-toluenesulfonic acid
m-CPBA=m-Chloroperbenzoic acid
TMAD=N,N,N',N'-tetramethylazodicarboxamide
CSA=camphorsulfonic acid
NaHMDS=sodium hexamethyl disilylazide
HRMS=High Resolution Mass Spectrometry
HPLC=High Performance Liquid Chromatography
LRMS=Low Resolution Mass Spectrometry
nM=nanomolar
Ki=Dissociation Constant for substrate/receptor complex
pA2=−logEC$_{50}$, as defined by J. Hey, *Eur. J. Pharmacol.*, (1995), Vol. 294, 329–335.
Ci/mmol=Curie/mmol (a measure of specific activity)
Tr=Triphenylmethyl
Tris=Tris(hydroxymethyl)aminomethane

Example 1

Preparation of 1-trityl-4-chloromethyl Imidazole (2)

(i) Preparation of compound (1):

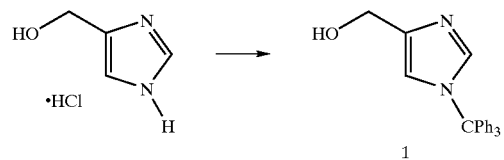

Commercially available 4-hydroxymethyl imidazole hydrochloride (from Aldrich Chemical Company, Milwaukee, Wis.) and triphenyl methyl chloride were reacted according to literature procedure (Kelley, *J. Med. Chem.*, 20 (5), 721 (1977) to afford compound (1).

(ii) Preparation of compound (2):

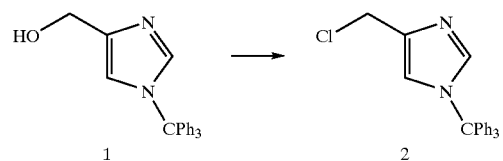

To a stirred suspension of compound (1) (3.15 g, 9.16 mmol) in anhydrous toluene (50 ml) at 0° C. was added triethylamine (2.7 ml, 18.3 mmol) and thionyl chloride (1.6 g, 13 mmol). After stirring at 0° C. for 1 h, the mixture was poured onto ice water with stirring. Extraction with ethyl acetate and subsequent concentration of solvents produced compound (2) (mp 88–91° C.). FABMS m/z 359 (MH$^+$).

Example 2

Preparation of Compound (4)

Compound (2) (0.3588 g, 1.0 mmol) from Example 1 and 1-[(4-Chlorophenyl)-pyridin-2yl-methyl]-piperazine (3) (0.2878 g, 1.0 mmol) (disclosed in U.S. Pat. No. 5,432,175) were dissolved in CH$_2$Cl$_2$(2.5 ml). Triethylamine (0.14 ml) was added and the reaction mixture was stirred overnight at room temperature. The solvent was concentrated and the

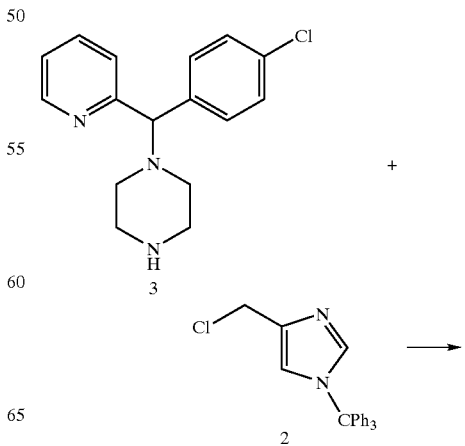

-continued

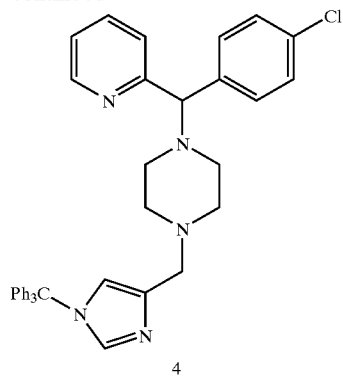

4 crude product was purified on flash silica eluting with 1–2% methanol saturated with ammonia:CH₂Cl₂ to afford the title compound (4) as a white foam.

Example 3

Preparation of Compound (5)

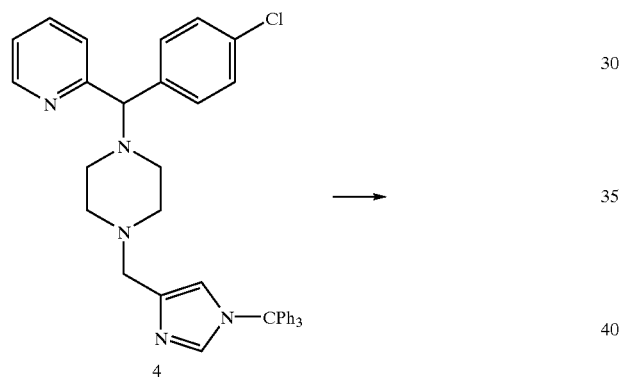

Compound (4) (0.191 g, 0.313 mmol) from Example 2 was treated with 0.5N HCl (40 ml) and refluxed for 0.5 h. The reaction mixture was washed several times with ether and concentrated to a yellow solid. The solid was redissolved in H₂O (10 ml), neutralized, and extracted with CH₂Cl₂. Concentration of the organic layer to dryness afforded the title compound (4) as a yellow solid. MS(FAB) 368 (MH⁺).

Example 4

Preparation of Compound (7)

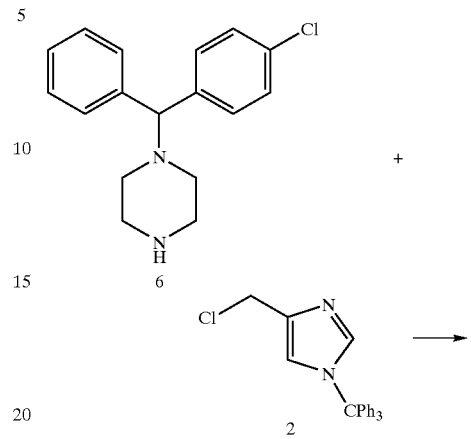

Using a similar procedure as in Example 2, substituting with 1-(4-Chlorobenzhydryl)piperazine (6) (from Aldrich Chemicals, 1.0 g, 3.49 mmol) followed by detritylation as in Example 3 afforded the title compound (7) as a solid.

Example 5

Preparation of Compound (10)

1-(1H-Imidazol-4-ylmethyl)-piperazine hydrochloride(8) (described in WO 93/12093) (0.2835 g, 1 mmol) was dissolved in methanol (5 ml). 1.0N KOH/Methanol (1 ml) was added and stirred at room temperature for 0.5 h. 3,3-Diphenylpropionic acid(9) (Aldrich) (0.226 g, 1 mmol), 1-(3-dimethylaminopropyl)-3-ethylcarbodiimide hydrochloride (Aldrich) (0.192 g, 1 mmol), and 1-hydroxybenzotriazole hydrate (Aldrich) (0.135 g, 1 mmol) were added and the mixture stirred overnight at room temperature. The

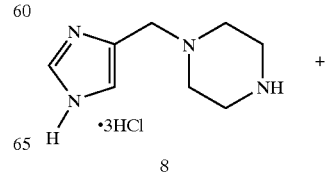

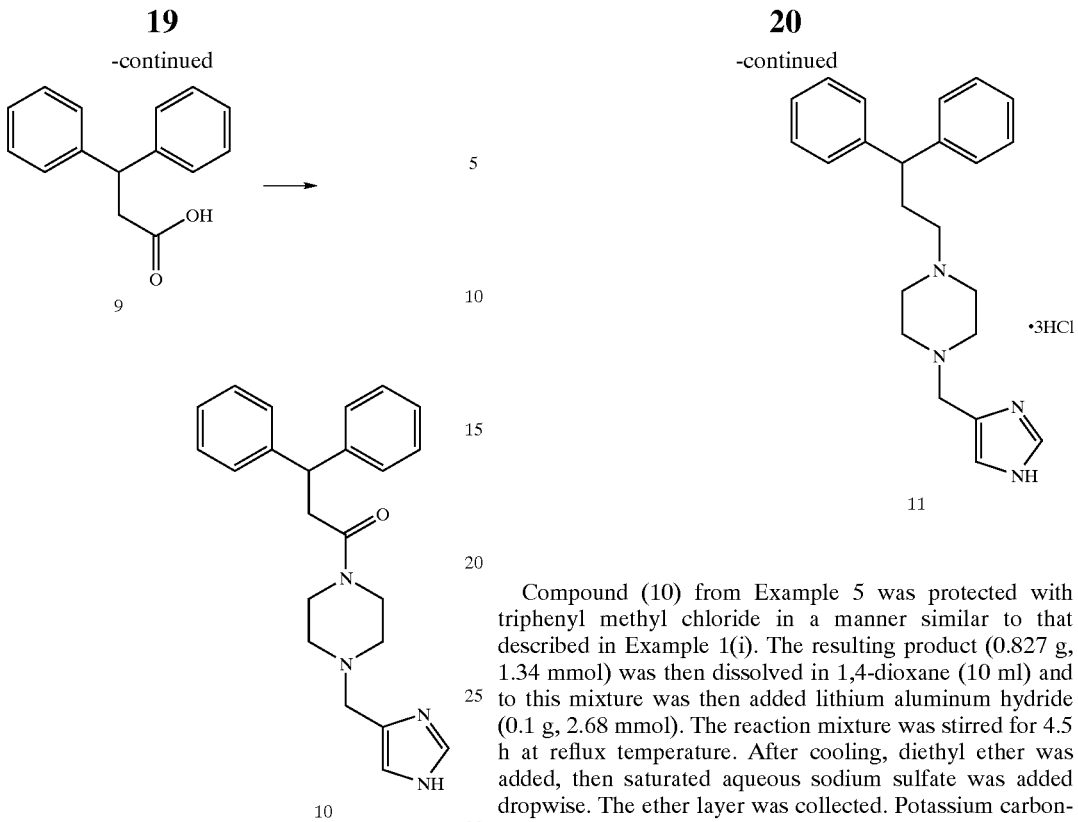

reaction mixture was concentrated, and the residue was dissolved in H₂O, the pH was adjusted to 8 and the aqueous solution was extracted with CH₂Cl₂. The organic layer was dried over K₂CO₃/Na₂SO₄, filtered and concentrated. Purification by preparative thin layer chromatography afforded the title compound (10).

Example 6

Preparation of Compound (11)

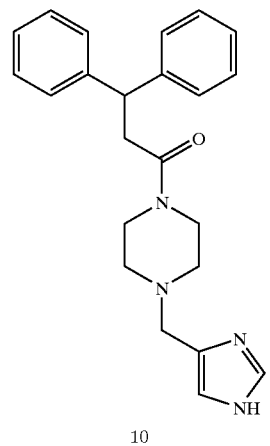

Compound (10) from Example 5 was protected with triphenyl methyl chloride in a manner similar to that described in Example 1(i). The resulting product (0.827 g, 1.34 mmol) was then dissolved in 1,4-dioxane (10 ml) and to this mixture was then added lithium aluminum hydride (0.1 g, 2.68 mmol). The reaction mixture was stirred for 4.5 h at reflux temperature. After cooling, diethyl ether was added, then saturated aqueous sodium sulfate was added dropwise. The ether layer was collected. Potassium carbonate was added to the aqueous layer, which was extracted with ethyl acetate. The organic layers were combined, dried over potassium carbonate and sodium sulfate, filtered and concentrated. Purification by flash column chromatography eluting with 0.5%–2% methanol saturated with ammonia:CH₂Cl₂ afforded the product as a white powder. This product was then stirred with 1N HCl (25 ml) at 95° C. for 1 h. After cooling, the mixture was extracted with ethyl ether, and the aqueous layer was concentrated under vacuum. The residue was dissolved in methanol, concentrated, then recrystallized from methanol/ethyl ether to afford the title compound (11) as the HCl salt.

Example 7

Preparation of Compound (14)

(i) Preparation of compound (13):

Calcium oxide (0.12 g, 2.2 mmol) was added to a solution of 1-[(4-Chlorophenyl)-pyridin-2yl-methyl]-piperazine(3) in DMF (3 ml) at room temperature. 4-(3-chloropropyl) imidazole(12) (prepared as reported by G. J. Durant et al., *J. Med. Chem.*, 28 (10), pp. 1414–1422. (1985)) (0.39 g, 1 mmol) was added and the mixture heated to 65° C. for 5 days. The reaction was cooled to room temperature and diluted with ether. Celite was added

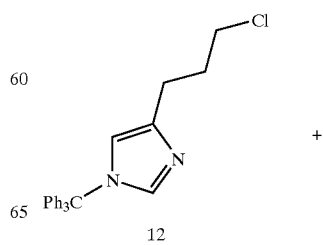

-continued

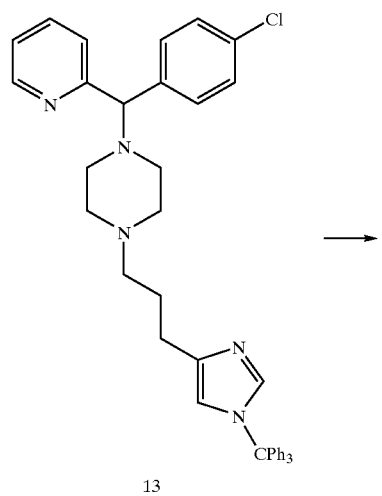

3

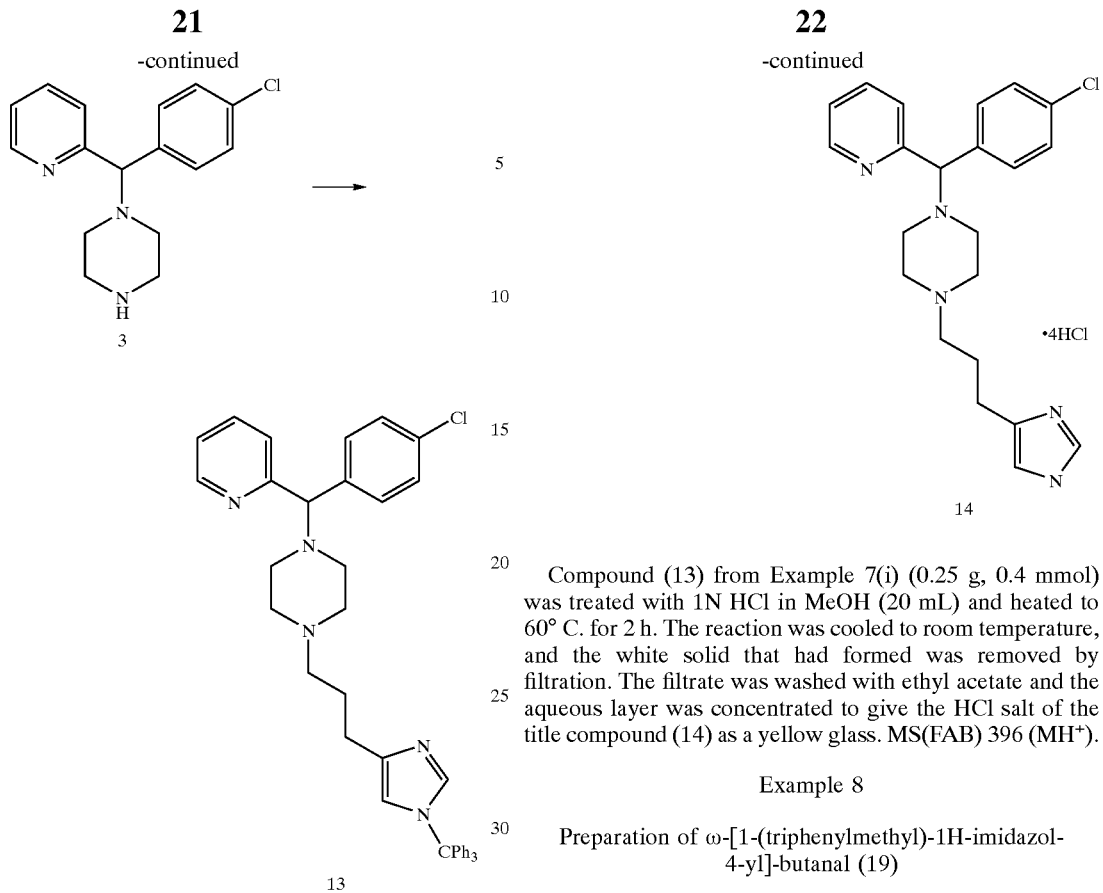

13 and the mixture was filtered. The filtrate was poured into water and extracted twice with ether. The combined organics were washed with water and brine and dried over magnesium sulfate. Concentration gave a tan foam which was chromatographed on a silica gel column (5% MeOH/NH₃ in CH₂Cl₂) to give compound (13) as a white solid. MS(FAB) 638 (MH⁺).

(ii) Preparation of compound (14):

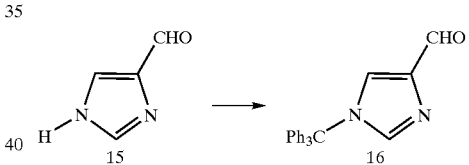

13

-continued

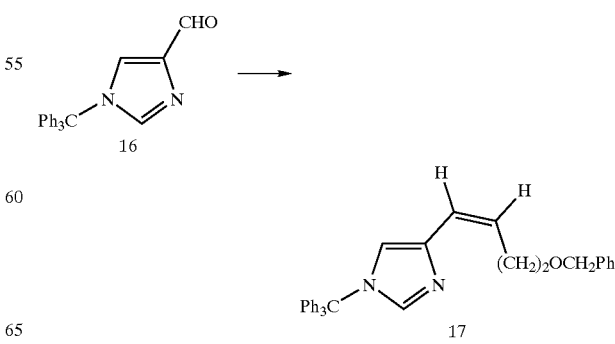

14

Compound (13) from Example 7(i) (0.25 g, 0.4 mmol) was treated with 1N HCl in MeOH (20 mL) and heated to 60° C. for 2 h. The reaction was cooled to room temperature, and the white solid that had formed was removed by filtration. The filtrate was washed with ethyl acetate and the aqueous layer was concentrated to give the HCl salt of the title compound (14) as a yellow glass. MS(FAB) 396 (MH⁺).

Example 8

Preparation of ω-[1-(triphenylmethyl)-1H-imidazol-4-yl]-butanal (19)

(i) Preparation of 1-(triphenylmethyl)-1H-imidazol-4-carboxaldehyde (16):

Commercially available 4-imidazole carboxaldehyde (15) (from Maybridge Chemical Company, Cornwall, U.K.) (35.0 g, 364 mmol) was reacted according to literature procedure (Kelley, *J. Med. Chem.* 20 (5), 721 (1977)] to afford the desired tritylated product (16) as an off-white solid. mp.186.5–194° C. Trituration of this product with ether yielded a cream-colored powder with mp 195–197° C.

(ii). Preparation of 4-[(Z)-4-(phenylmethoxy)-1-butenyl]-1-(triphenylmethyl)-1H-imidazole (17):

To a mechanically stirred solution of the aldehyde (16) (19.65 g, 58.1 mmol) in dry tetrahydrofuran (1 L), was added (3-benzyloxypropyl)triphenyl phosphonium bromide (30.02 g, 61.1 mmol). The resulting suspension was cooled to 15° C., and then a 1.0M solution (61.4 mL; 61.4 mmol) of potassium t-butoxide in tetrahydrofuran was added over five minutes. The reaction mixture was allowed to warm to room temperature and was stirred for 2 h. The reaction mixture was filtered through Celite; the filter cake was washed with tetrahydrofuran (2×150 mL); the filtrate and washings were combined, diluted with ether (800 mL) and refiltered through fresh Celite. The filtrate was concentrated under vacuum, and the residue was chromatographed on silica gel, eluting with a gradient of hexanes-ethyl acetate (3:1 to 2:1), to obtain the title compound (17) as a pale yellow powder, mp 101–104° C. MS(FAB) 471 (MH$^+$).

(iii). Preparation of 1-(triphenylmethyl)-1H-imidazole-4-butanol (18):

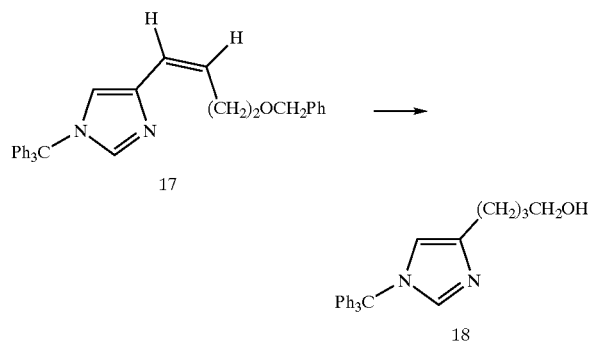

A mixture of the olefinic ether (17) (18.27 g, 38.8 mmol) in anhydrous ethanol (350 mL), 1.0M ethereal hydrochloric acid (38.8 mL, 38.8 mmol) and 10% palladium-on-carbon catalyst was hydrogenated at 48 psi for 30 min. on a Parr shaker. It was then filtered through celite and the filter cake was washed with methanol. The combined filtrate and washings were concentrated and dried under high vacuum to obtain the title compound (18) as an off-white solid. MP 144–146° C.

(iv) Preparation of ω-[1-(triphenylmethyl)-1H-imidazol-4-yl]-butanal (19):

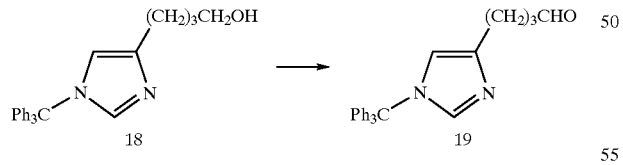

In a dry flask equipped to provide an inert gas atmosphere, a solution of oxalyl chloride (2.18 mL, 25.0 mmol) in dry dichloromethane (50 mL) was prepared and cooled to −60° C. in a CO$_2$-acetone bath. A solution of dimethylsulfoxide (3.60 mL, 50.7 mmol) in dry dichloromethane (10 mL) was added dropwise over 5–10 min., while maintaining the reaction temperature at −55 to −60° C. It was stirred an additional 5 min at −60° C.; then a solution of compound (18) (8.67 g, 20.7 mol) in dry dichloromethane (140 mL) was added over 15–20 minutes, maintaining reaction temperature in the range of −55 to −60° C. Stirring of the mixture was continued at −60° C. for one hour; then neat triethylamine (17.6 mL, 12.6 mmol) was added at a rate such that the reaction temperature was maintained at −55 to −60° C. The reaction was stirred for 5 min. at this temperature, the cooling bath was removed, and stirring continued at room temperature for 1.5 h. The reaction mixture was washed with water (4×50 mL), then brine (75 mL); dried over anhydrous magnesium sulfate; and solvent removed under vacuum to obtain a viscous oil. If triethylamine hydrochloride remained, the residual oil was dissolved in diethyl ether (100 mL), washed with water (1×30 mL; 2×10 mL), then with brine (30 mL), and dried over anhydrous magnesium sulfate. The solvent was removed under vacuum to obtain the title aldehyde (19) as a viscous yellow oil, sufficiently pure for further use. MS(FAB) 381 (MH$^+$).

Example 9

Preparation of Compound (23)

(i) Preparation of compound (20):

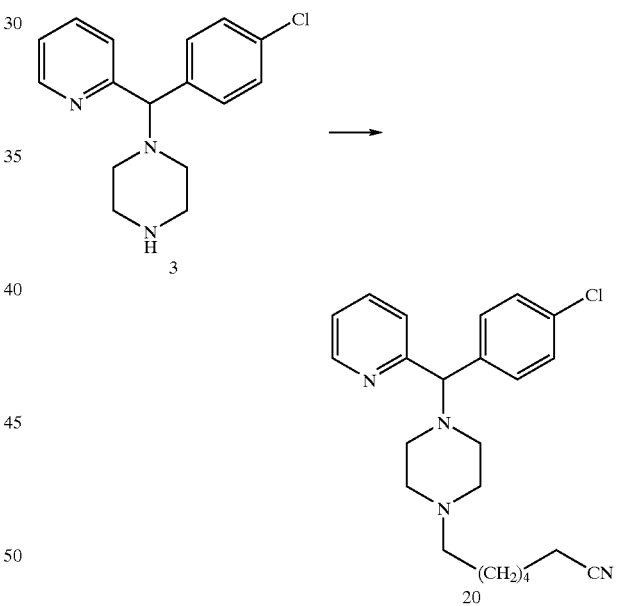

A solution of 1-[(4-Chlorophenyl)-pyridin-2-yl-methyl]-piperazine(3) (1.44 g, 5 mmol) in dry acetonitrile (15 mL) was treated with solid potassium carbonate (2.07 g, 15 mmol) and 7-bromo heptanenitrile (from Aldrich) (0.95 g, 5 mmol). The reaction was heated to 90° C. for 20 h. The reaction was cooled to room temperature, diluted with water (25 mL) and extracted with toluene (2×50 mL). The combined organic layers were washed with water, brine and dried over sodium sulfate. Concentration of the solvent layer afforded an oil which was purified on a flash column (5% MeOH/NH$_3$ in CH$_2$Cl$_2$) to give compound (20) as a tan oil.

(ii) Preparation of compound (21):

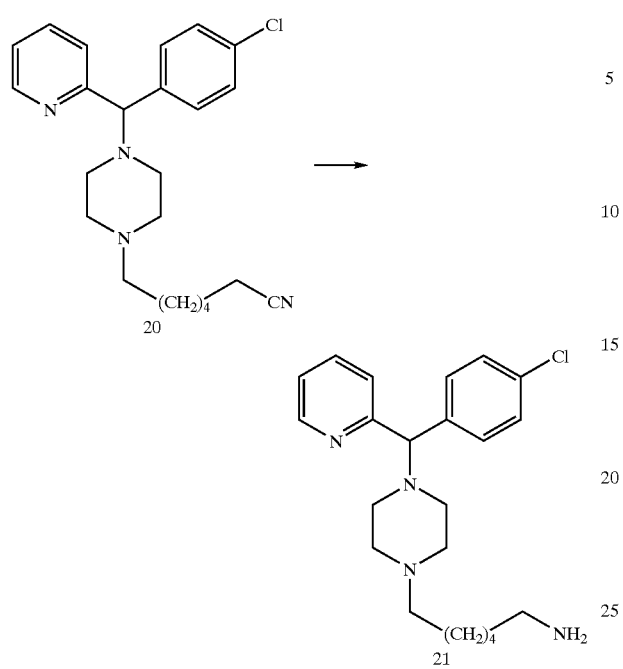

Compound (20) was reacted in a similar manner as described in *Arch. Phar.* 1996, 329, 87, to afford compound (21). MS(FAB) 401 (MH⁺).

(iii) Preparation of compound (22):

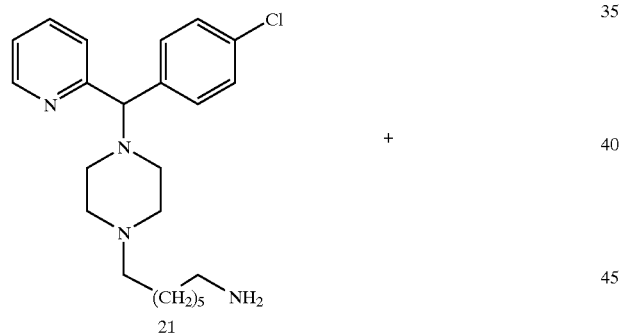

Compound (21) (0.4 g, 1 mmol), the imidazole-butyraldehyde (19) (0.38 g, 1 mmol) and 3Å molecular sieves (0.8 g) were stirred at room temperature in trifluoroethanol (15 mL) for 2 h. Sodium triacetoxyborohydride (from Aldrich) was added and the reaction stirred for 20 h. The sieves were then removed by filtration and the filtrate concentrated. The residue was purified on a silica gel column (5%–10% MeOH/NH₃ in CH₂Cl₂) to give compound (22) as an oil. MS(FAB) 765 (MH⁺).

(iv) Preparation of compound (23):

In a manner similar to that described in Example 7 (ii), compound (22) (0.34 g, 0.46 mmol) was deprotected to give the HCl salt of the title compound (23). MS(FAB) 523 (MH⁺).

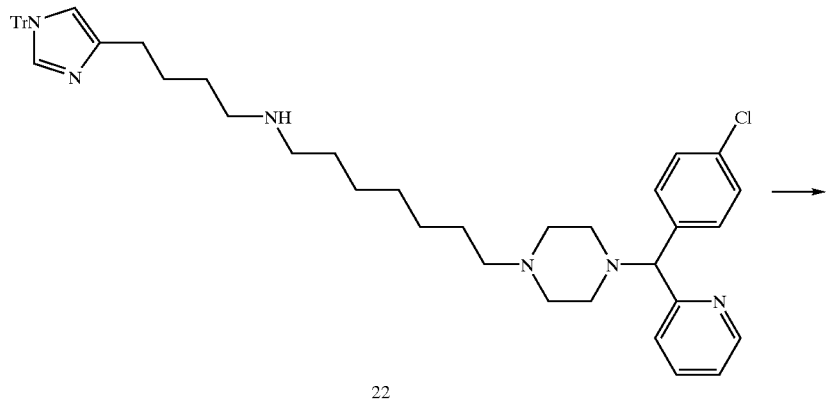

23

Example 10

Preparation of Compound (28)

(i) Prepration of compound (26):

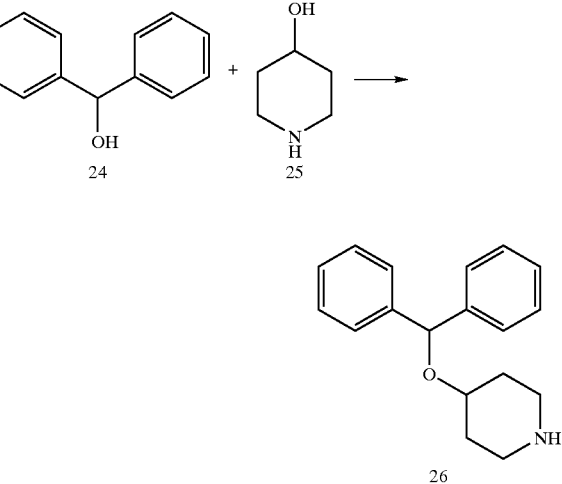

A solution of compound (24) (available from Aldrich) (2.75 g, 15 mmol), 4-hydroxypiperidine (25) (from Aldrich) (1.52 g, 15 mmol), and p-toluenesulfonic acid (3.04 g, 16 mmol) in toluene (50 mL) was heated to reflux with azeotropic removal of the water using a Dean-Stark trap. When complete, the reaction was cooled to room temperature and washed with 10% NaOH, water, and brine, and dried over magnesium sulfate. Concentration afforded an amber oil (3.57 g) which was dissolved in ether (75 mL) and treated with 1N HCl in ether (20 mL). A white precipitate formed which was collected by filtration and dried under vacuum affording compound (26) as a white solid. MS(Cl) 268 (MH$^+$).

(ii) Preparation of compound (28):

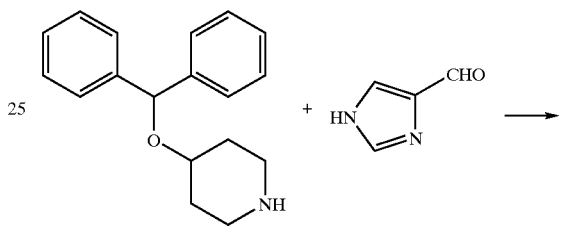

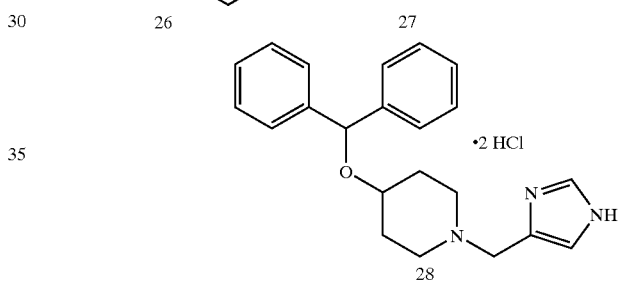

Compound (26) (0.61 g, 2 mmol) was reacted in a manner similar to that described in Example 9(iii), substituting 4-imidazole carboxaldehyde (27) (from Maybridge). The product was stirred with 1N HCl in methanol at 60° C. for 2 h and then was concentrated and washed with ethyl acetate to give the HCl salt of compound (28) as a white solid. MS(FAB) 348 (MH$^+$).

Example 11

Preparation of Compound (31)

(i) Preparation of compound (30):

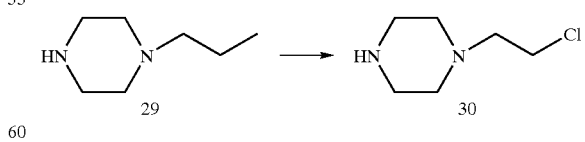

A stirred suspension of the hydrochloride salt of 1-(2-hydroxyethyl) piperazine(29) (170 g, 1.02 mol) and thionyl chloride (190 ml) was heated under reflux for 5 h and then concentrated. The solid residue was triturated with ether and filtered to give compound (30) as the hydrochloride salt. MS(Cl) 149 (MH$^+$).

(ii) Preparation of compound (31):

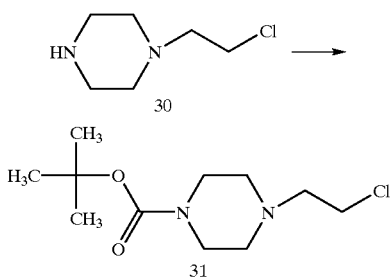

To a cooled (ice bath) suspension of sodium carbonate (240 g, 2.86 mol) in water (800 ml) was added portionwise the entire quantity of compound (30) obtained from step (i) above and stirred for 1 h. Then di-tert-butyl dicarbonate (300 g, 1.38 mol) in $CH_2Cl_2$ (1 L) was added and the mixture was stirred at room temperature overnight. The organic layer was separated, washed with brine, dried over magnesium sulfate and concentrated to an oil which crystallized in cold hexane to afford compound (31). MS(FAB) 249 ($MH^+$), MP 62–64° C.

Example 12

Preparation of Compound (36)

(i) Preparation of compound (33)

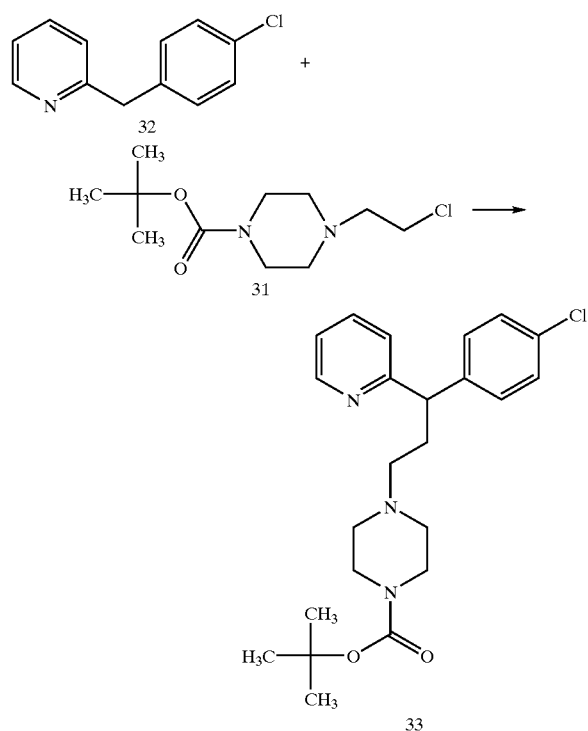

To a stirred suspension of sodamide [prepared from metallic sodium (1.5 g) in liquid ammonia] in liquid ammonia (300 ml) at approximately −40° C. was added dropwise a solution of 2-(4-chlorobenzyl)pyridine (32) (from Aldrich) (10.2 g, 0.05 mol) in THF (15 ml) over 15 min. Then a solution of compound (31) (15 g, 0.06 mol) in THF (50 mL) was added. The mixture was stirred and allowed to warm up to room temperature over 18 h. The residue was treated with saturated aqueous ammonium chloride (50 ml) and extracted with ether. The combined extracts were dried over anhydrous $Na_2SO_4$ and concentrated. The residue was purified by silica gel column chromatography eluting with ethyl acetate to produce compound (33) as a syrup. MS(FAB) 416 ($MH^+$).

(ii) Preparation of compound (34):

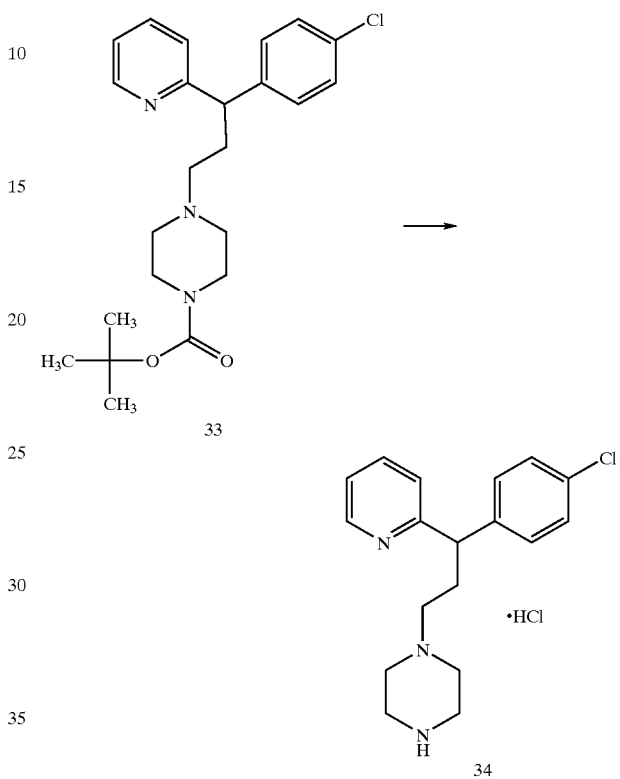

A solution of compound (33) (6.5 g, 0.014 mol) in methanol (60 mL) and 15% HCl (aqueous) (60 ml) was heated under reflux for 18 h. Concentration of the mixture afforded the HCl salt of compound (34). MS(Cl) 316 ($MH^+$), MP 220–230° C.

(iii) Preparation of compound (35):

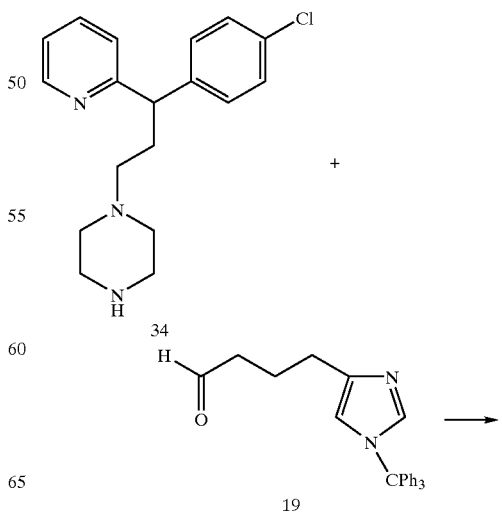

31

-continued

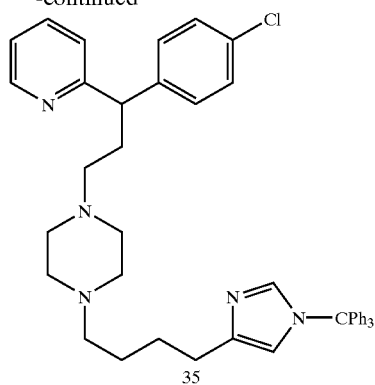
35

To a solution of compound (34) (1.0 g, 2.35 mmol) in methanol (20 ml) was added ground sodium hydroxide (0.25 g, 6.25 mmol), followed by 2 drops of acetic acid, a solution of compound (19) from Example 8(iv) (0.89 g, 2.3 mmol) in 1,1,1-trifluoroethanol (40 mL), and sodium cyanoborohydride (0.11 g, 1.77 mmol). After stirring for two days, the mixture was filtered and concentrated. The residue was basified with 1N sodium hydroxide and extracted with ether. The combined organic extracts were washed with brine, dried over magnesium sulfate and concentrated. The crude product was purified by flash silica gel chromatography eluting with (1:4) methanol:ethyl acetate to afford compound (35) as a syrup. MS(Cl) 680 (MH$^+$).

(iv) Preparation of compound (36):

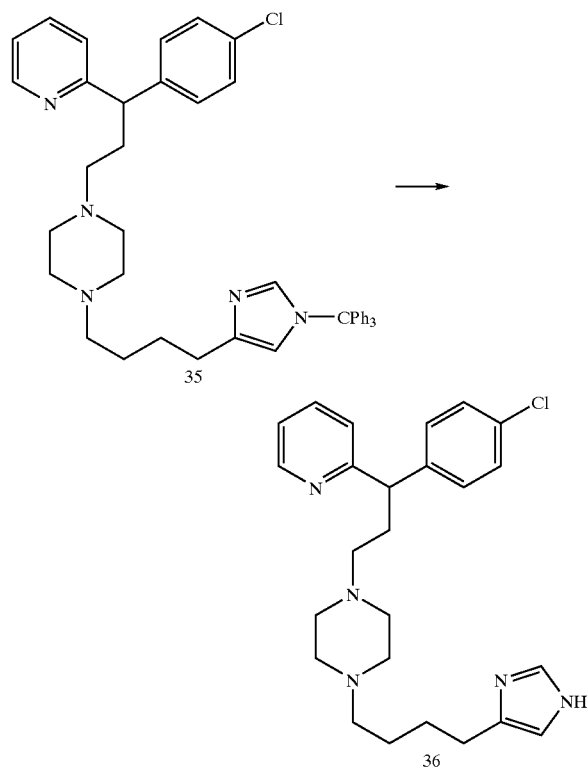

A solution of compound (35) (0.96 g, 1.41 mmol) in 15% aqueous HCl (20 mL) and methanol (20 mL) was heated under reflux for 1 h. Concentration, and subsequent filtration and washing with ether afforded the HCl salt of compound (36). MP 225–230° C.

32

Example 13

Preparation of Compound (39)

(i) Preparation of compound (38):

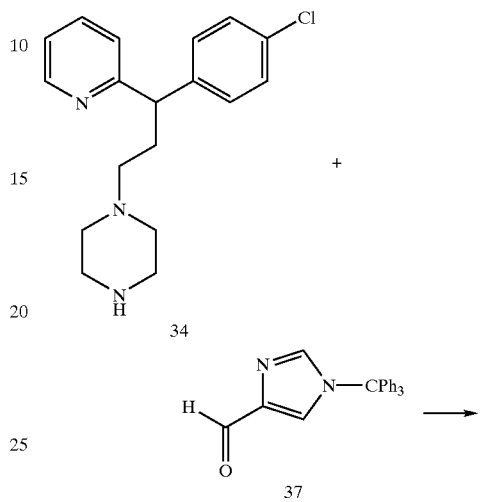

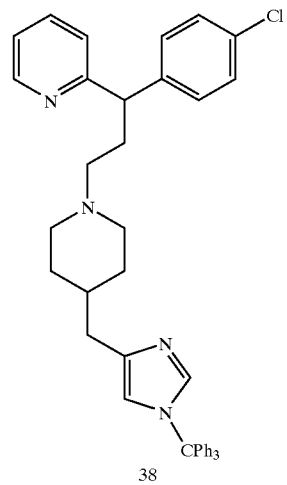
38

To a solution of compound (34) (1.0 g, 2.35 mmol) in methanol (15 mL) was added ground potassium hydroxide (0.08 g, 1.42 mmol), followed by 4-imidazol-carboxaldehyde(37) (from Maybridge) (0.8 g, 2.35 mmol), magnesium sulfate (1.0 g) and a solution of sodium cyanoborohydride (0.145 g, 2.3 mmol) in methanol (10 mL). After stirring for 48 h, the reaction was filtered and concentrated. The residue was basified with 0.5N sodium hydroxide. The precipitate was filtered and purified by flash silica gel column chromatography eluting with 5:95 methanol:CH$_2$Cl$_2$ affording the title compound (38) as a solid. MS(FAB) 638 (MH$^+$).

(ii) Preparation of compound (39):

Compound (38) was reacted in a manner similar to that described in Example 12 (iv) affording the HCl salt of compound (39). MS(Cl) 396 (MH$^+$), MP 220–230° C.

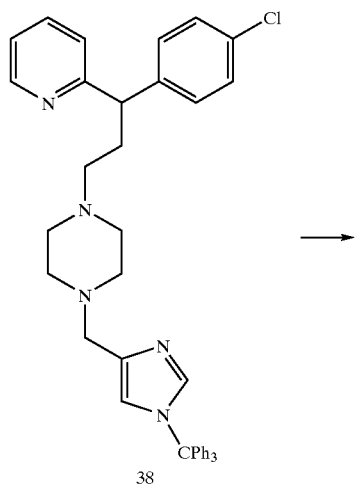

38

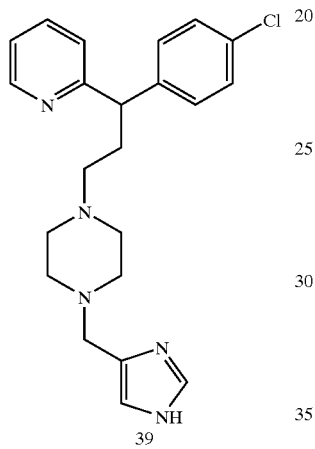

39

Example 14

Preparation of Compound (45)

(i) Preparation of compound (41):

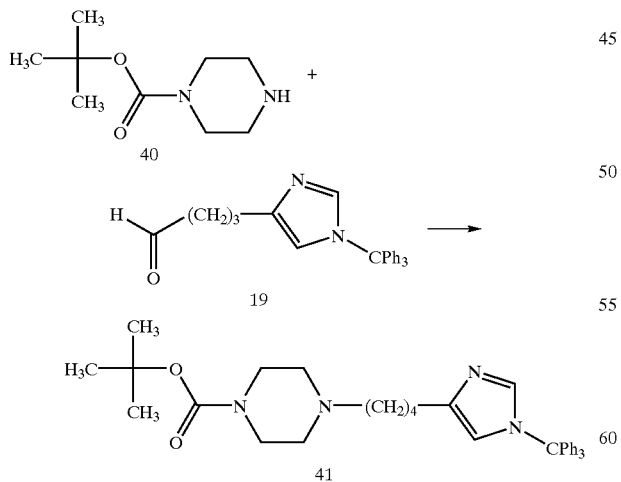

To a stirred solution of t-butyloxycarbonyl-piperazine(40) (from Aldrich) (2.6 g, 0.014 mol) and compound (19) in 1,1,1-trifluoroethanol (60 mL) were added 3Å molecular sieves (7 g) and sodium cyanoborohydride (0.87 g, 0.014 mol). After stirring at room temperature for 20 h, the reaction was filtered and concentrated. The residue was basified with saturated sodium bicarbonate and extracted with ethyl acetate. The extracts were washed with brine, dried over magnesium sulfate, filtered and concentrated to a syrup. Further purification by flash silica gel column chromatography eluting with 3–10% methanol/ethyl acetate afforded compound (41) as a glass. MS(FAB) 551 (MH$^+$).

(ii) Preparation of compound (42):

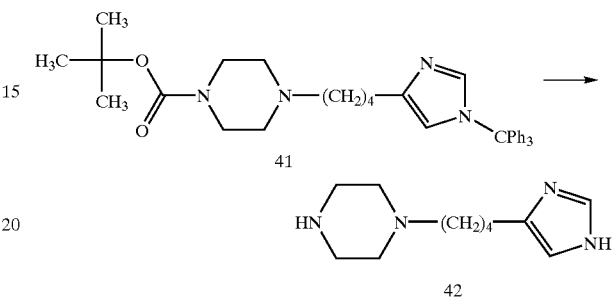

Compound (41) was reacted in a manner similar to that described in Example 12 (iv) affording the HCl salt of compound (42). MS(Cl) 209 (MH$^+$), MP 290–300° C.

(iii) Preparation of compound (43):

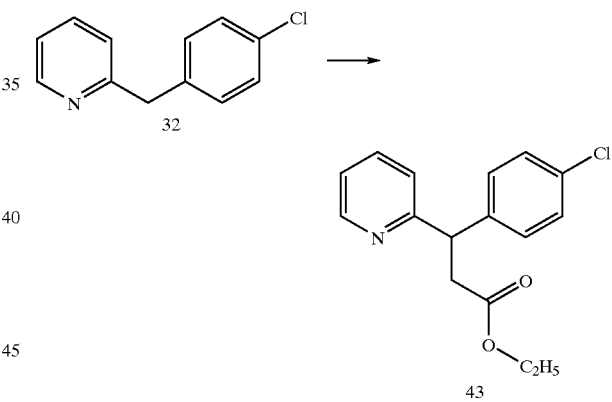

To a stirred suspension of sodamide (1.1 mol) in liquid ammonia (1.5 L) at approximately −40° C., was added 2-(4-chlorobenzyl)-pyridine(32) (from Aldrich) (203.5 g, 1 mol) followed by ethyl bromoacetate (168.0 g, 1 mol). The mixture was stirred and warmed up to room temperature as excess ammonia evaporated. The residue was treated with water and extracted with ether. Combined ether extracts were concentrated and the oil residue was distilled to produce compound (43) as a brown oil. BP 168–180° C.

(iv) Preparation of compound (44):

Compound (43) (90.5 g, 0.31 mol) and a solution of potassium hydroxide (45 g, 0.8 mol) in ethanol (1.2 L) were refluxed for 3 h. Concentration and trituration of the residue with 2% aqueous HCl (1.6 L) afforded compound (44). MP 179.5–180.5° C.

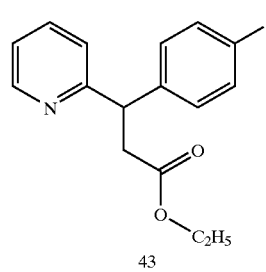

43

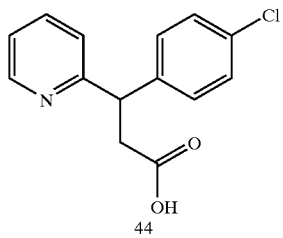

44

(v) Preparation of compound (45):

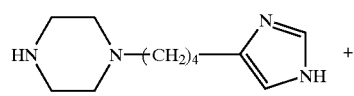

42

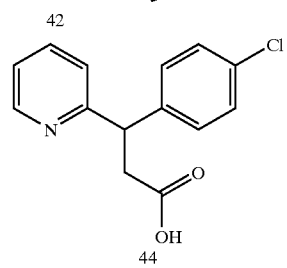

44

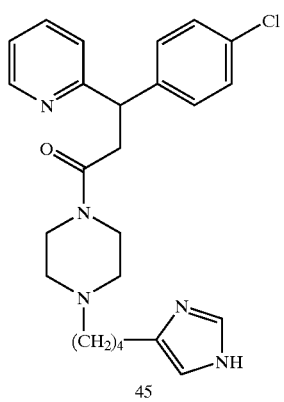

45

To a suspension of compound (42) (1.7 g, 5.1 mmol) in CH₂Cl₂ (60 ml) and DMF (15 ml) at −10° C., were added N,N-diisopropylethyl-amine (3.7 g, 28.7 mmol), compound (44) (1.4 g, 5.35 mmol), 1-hydroxybenzotriazole (from Aldrich) (0.73 g, 5.35 mmol) and 1-(3-dimethylaminopropyl)-3-ethylcarbodiimide hydrochloride (1.1 g, 5.7 mmol). After stirring at room temperature for 18 h, the reaction was diluted with CH₂Cl₂, washed with 2% NaHCO₃ and water. The organic layer was dried over magnesium sulfate and concentrated to an oil. Further purification by flash silica gel column chromatography eluting with (90:8:0.5) CH₂Cl₂:methanol:28% ammonium hydroxide afforded compound (45) as a glass. MS(Cl) 452 (MH⁺).

Example 15

Preparation of Compound (46)

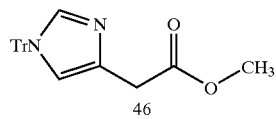

46

The preparation of compound (46) is described by N-Y. Shih et al.; *Bioorg. Med. Chem. Lett.* (1998) 8; 243–248.

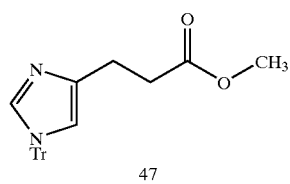

47

Example 16

Preparation of Compound (47)

The preparation of compound (47) is described by Clitherow et al. *Bioorg. Med. Chem. Lett.* 1996, 8, 833–838, was tritylated as in Example 1 to provide compound (47).

Example 17

Preparation of Compound (50)

4-(1-Trityl-1H-imidazol-4-yl)-butylamine(49) (R. Wolin et al, *Bioorg. Med. Chem. Lett.* (1998) 8, 2157–2162. (0.125 g, 0.9 mmol) was detritylated in the same manner as Example 7(ii) and reacted with commercially available (from Jensen Chemical Limited, London, United Kingdom) cetirizine (48) (0.402 g, 0.99 mmol) in a similar manner as described in Example 14(v). The product was dissolved in ethyl acetate

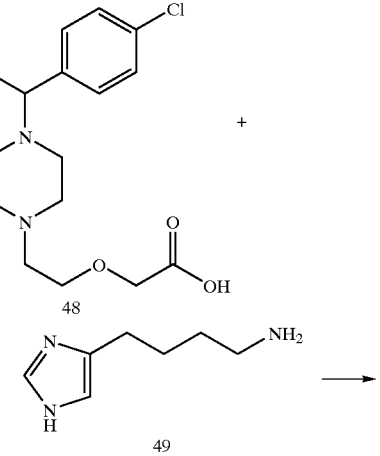

48

49

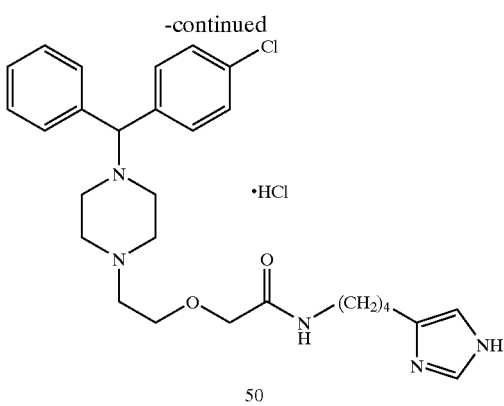

(20 ml) then treated with 1M HCl/Et₂O (1.26 mL). Trituration and vacuum concentration afforded the HCl salt of the title compound (50) as a tan powder. HRMS: (MH⁺) 510.2625/510.2636.

Example 18

Preparation of Compound (52)

(i) Preparation of Compound (51).

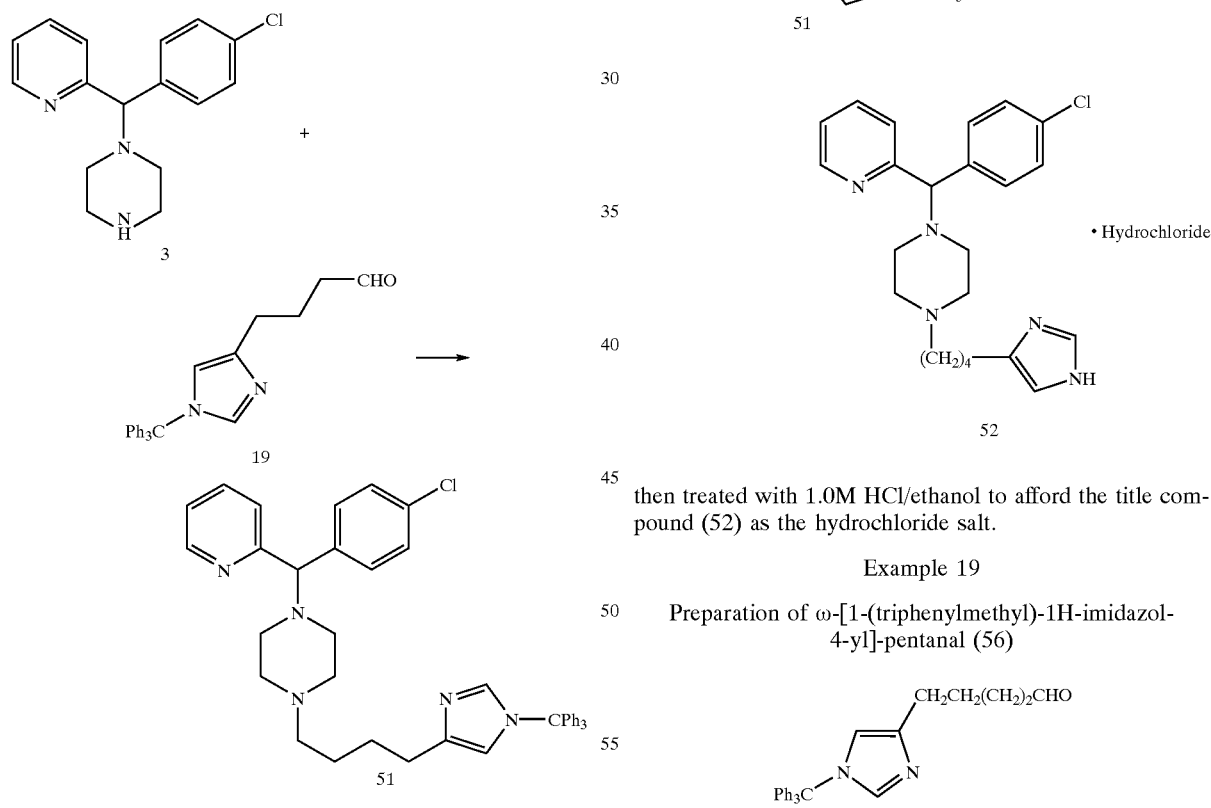

Compound (19) (0.409 g, 1.076 mmol) and 1-[(4-chlorophenyl)-pyridin-2yl-methyl]-piperazine (3) (0.310 g, 1.076 mmol) were dissolved in methanol (20 ml). Methanesulfonic acid (69.8 microliters, 1.076 mmol), magnesium sulfate (0.259 g, 2.15 mmol), and 3Å molecular sieves (0.260 g) were successively added and stirred at room temperature for 0.5 h. Then a solution of sodium cyanoborohydride in methanol (20 ml) was added in one portion via syringe. The resulting mixture was stirred for 3 h at room temperature. The reaction was then filtered through a pad of celite and partitioned between CH₂Cl₂ and 1.1M NaHCO₃. The organic layer was extracted and washed with water, then with brine, filtered through Na₂SO₄ and concentrated to an off-white semisolid. The product was further purified by flash silica column chromatography eluting with CH₂Cl₂:MeOH:NH₄OH (95:5:0.5) to afford the title compound (51) as a pale pink powder. MS (MH⁺) 652.

(ii). Preparation of Compound (52):

Compound (51) from Example 24 (i) above was detritylated in a manner similar to that described in Example 12(iv). The crude product was chromatographed over silica gel, eluting with CH₂Cl₂-MeOH-NH₄OH (92.5:7.5:0.5) to obtain the free base form of compound (52) which was

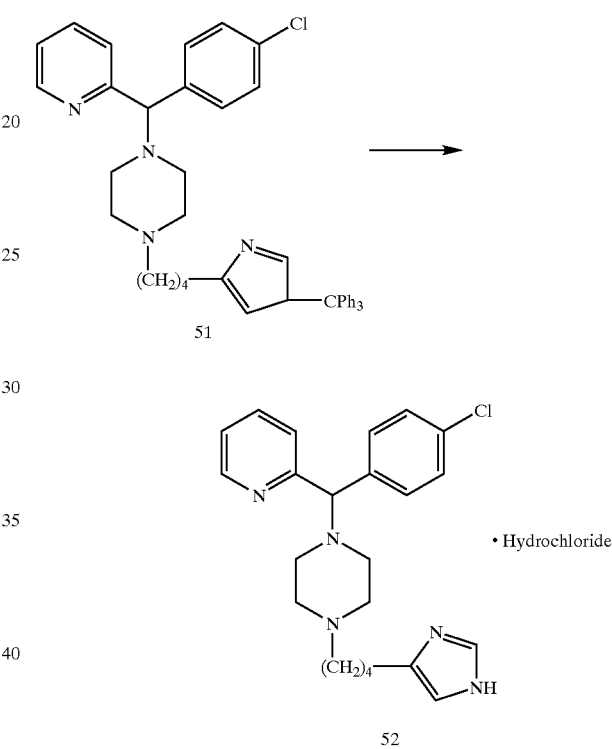

then treated with 1.0M HCl/ethanol to afford the title compound (52) as the hydrochloride salt.

Example 19

Preparation of ω-[1-(triphenylmethyl)-1H-imidazol-4-yl]-pentanal (56)

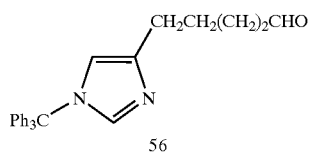

(i) Preparation of (ethoxycarbonylprop-1-yl)triphenyl phosphonium bromide (53):

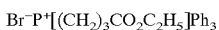

A mixture of triphenylphosphine (24.6 g; 0.0936 mol) and ethyl 4-bromobutyrate (from Aldrich) (14.4 mL; 0.101 mol) was heated from room temperature to 105° C. over a period of 15–20 minutes; then heating was continued at 105° C. for 10 minutes. The solution was allowed to cool, but while still warm, diethyl ether (50 mL) was cautiously added via a condenser. The resultant gum was triturated to obtain a white powder. Ether was decanted, fresh diethyl ether (50 mL) was added, and trituration continued for 10 min. The reaction mixture was filtered, the filter cake washed with diethyl ether, and then solvent was removed under vacuum from the combined filtrate and washings to obtain a mixture of oil and solids. This mixture was heated to 100° C.; was cautiously treated with diethyl ether (2×55 mL); and the trituration, filtration, and concentration sequence described above was repeated. The two batches of white solids obtained from this process were combined, triturated with toluene (150 mL), filtered, and the collected solids were washed with toluene and dried under high vacuum to obtain the title salt (53). FABMS 377 (M+) mp 177–179° C.

(ii) Preparation of ethyl 5-[1-(triphenylmethyl)-1H-imidazol-4-yl]-4-Z-pentenoate (54):

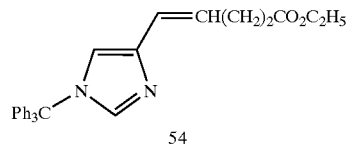
54

Under a nitrogen atmosphere, the triphenylphosphonium salt (53) (14.0 g, 0.0305 mol) was added to a stirred solution of aldehyde (16) (9.81 g, 0.029 mol) in tetrahydrofuran (500 mL). The resultant suspension was cooled to 0–5° C., 1M potassium t-butoxide in tetrahydrofuran (31 mL, 0.031 mol) was added over 3–5 min., and the mixture was stirred for 20 min. at 0–5° C. Celite was added to the reaction mixture, which was stirred briefly, filtered, and the filter cake washed with diethyl ether, followed by dichloromethane. The combined filtrate and washings were concentrated under vacuum. The residual oil was chromatographed on silica gel. Elution with a gradient of hexanes-ethyl acetate (3:1→2:1) yielded the title compound (54) as a white solid. FABMS 437 (MH+) mp 90–92.5° C.

(iii). Preparation of 5-[1-(triphenylmethyl)-1H-imidazol-4-yl]-4-Z-pentenal (55):

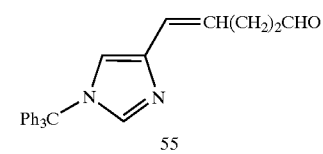
55

To a stirred solution of the ester compound (54) (671 mg, 1.54 mmol) in dry dichloromethane (12 mL) contained in a cold bath, was added a 1.0M solution of DIBAL-H in toluene (3.08 mL, 3.08 mmol) over approximately 4 min., while maintaining the reaction temperature at −55 to −60° C. After 8–10 min. of stirring at −58° C., the reaction was quenched by the addition of methanol (0.4 mL) and water (6 mL). The reaction mixture was allowed to warm to room temperature. The gelatinous precipitate that formed was removed by filtration through celite. The filter cake was washed with dichloromethane, and the combined filtrate and washings were dried over anhydrous magnesium sulfate. The drying agent was filtered, and evaporation of the solvent under reduced pressure yielded the title aldehyde (55) as a white powder. FABMS 393 (MH+); mp 117.5–120° C.

(iv) Preparation of ω-[1-(triphenylmethyl)-1H-imidazol-4-yl]-pentanal (56):

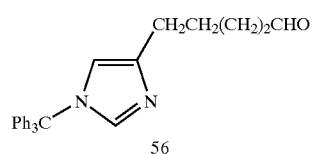
56

A mixture of the unsaturated aldehyde (5.42 g; 13.8 mmol) and 5% palladium-on-charcoal catalyst (0.50 g) in anhydrous methanol (130 mL) was hydrogenated for 30 min. at 30–35 psi on a Parr shaker. The catalyst was filtered through celite. Evaporation of the filtrate under reduced pressure and drying of the residue under high vacuum yielded the title compound (56) as a yellow viscous oil or glass sufficiently pure for further chemistry. FABMS 395 (MH+).

Example 20

Preparation of ω-[1-(triphenylmethyl)-1H-imidazol-4-yl]-hexanal (57)

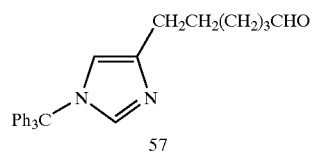
57

The title compound (57) was prepared in a manner similar to that described in Example 19 above, substituting 4-carboethoxybutyl triphenyl phosphonium bromide (from Lancaster Chemicals) for phosphonium salt (53) from Example 19, step (i).

In a manner similar to that described in Example 18, reacting 2-[(4-chlorophenyl)-piperidin-4-ylidene-methyl]-pyridine(58) (prepared according to John J. Piwinski et al. *J. Med. Chem.* 34(1) (1991) 457–461) with the appropriate aldehyde (from Examples 8, 19, or 20), the following compounds were prepared:

| Ex. # | Compound | name | ms (MH+) |
|---|---|---|---|
| 21 | 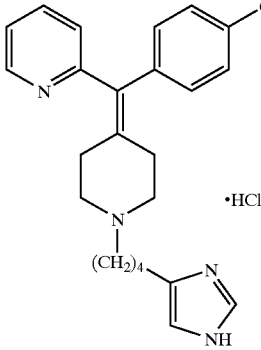 •HCl | 2-((4-Chloro-phenyl)-{1-[4-(1H-imidazol-4-yl)-butyl]-piperidin-4-ylidene}-methyl)-pyridine (72). | 407 |
| 22 | 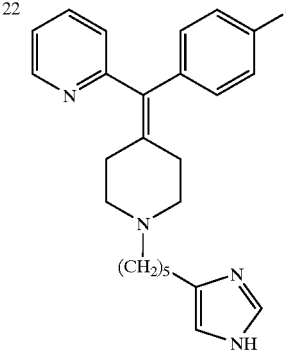 •HCl | 2-((4-Chloro-phenyl)-{1-[5-(1H-imidazol-4-yl)-pentyl]-piperidin-4-ylidene}-methyl)-pyridine (73). | 421 |
| 23 | 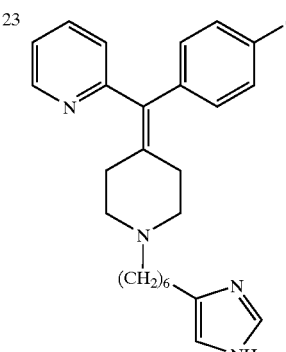 •HCl | 2-((4-Chloro-phenyl)-{1-[6-(1H-imidazol-4-yl)-hexyl]-piperidin-4-ylidene}-methyl)-pyridine (74). | 435 |

Example 24

Preparation of Compound (61)

(i) Preparation of compound (60):

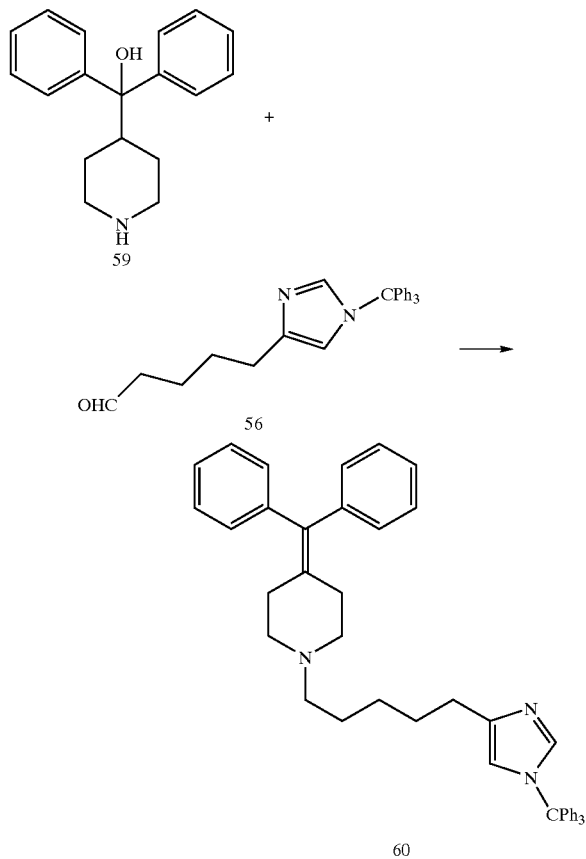

Diphenyl-4-piperidinomethanol (59) (from Maybridge Chemicals) (0.500, 1.87 mmol) was dissolved in 1,2-dichloroethanol (8.1 mL), and then ω-[1-(triphenylmethyl)-1H-imidazol-4-yl]-pentanal(56) (0.67 g, 1.70 mmol) was added. The reaction mixture was stirred for 2 min at room temperature before adding sodium triacetoxy borohydride (0.9 g, 4.25 mmol). After stirring for an additional 1.5 h, the reaction was quenched with sodium bicarbonate and extracted with EtOAC. The organic layers were combined, dried over magnesium sulfate, filtered and concentrated. The product was further purified by preparative thin layer chromatography, eluting with 5% MeOH:$CH_2Cl_2$.

(ii) Preparation of compound (61):

The trityl-N-protected product (60) from Example 24 (i) above was treated with 4M HCl in dioxane and refluxed for 8 h. The reaction was cooled and the solvent decanted off. Trituration with diethyl ether, followed by filtration, afforded the title compound (61) as the HCl salt. MS (Cl+/$CH_4$) 385.

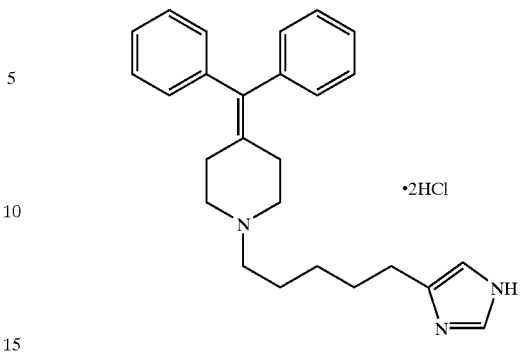

General Procedure for $H_1$-Receptor Binding Assay

The procedure used was based on that disclosed in V. T. Tran et al, "Histamine $H_1$ receptors identified in mammalian brain membranes with [H-3]mepyramine", *Proc. Natl. Acad. Sci. U.S.A.* 75 (1978) 6290–6294.

I. Tissue preparation protocol for histamine $H_1$ receptor binding assay:
1. The tissue source was male Sprague-Dawley rat brain. These were purchased stripped and frozen (available from Rockland Corporation, Gilbertsville, Pa.). The buffer used was ice-cold 50 mM Tris-HCl, pH 7.5. (The pH was determined at 25° C.)
2. The brains were spread out on plastic wrap on the benchtop and allowed to thaw for 10–15 min. After this, everything was kept ice-cold.
3. Two brains were put in each 50 ml round bottom centrifuge tube and 25 ml of buffer was added. Then they were broken up with a Polytron (from Brinkmann Instruments, Westbury, N.Y.) equipped with a PT-10 tip at setting 6 for 30 sec.
4. The volume in the tube was brought up to 45 ml and mixed and the particulate material was centrifuged at 1000×g (3000 rpm, SS-34 rotor) for 10 min to remove nuclei and unbroken cells.
5. Pellets were discarded and the supernatants were centrifuged 10 min at 50,000×g (20,000 rpm, SS-34 rotor).
6. The high-speed pellets were resuspended in a volume of Tris buffer equal to the original (4 ml), the contents of all tubes were pooled, and a sample was taken for BCA protein assay. The material was aliquotted, 45 ml per round-bottom tube, and the resuspension was recentrifuged. The yield of protein was approximately 20 mg/brain, so there was about 40 mg of protein per tube.
7. Pellets were frozen at −80° C.

II. $H_1$ Histamine receptor binding assay:
Materials: 96-well, deep-well, polypropylene plates, [$^3$H] pyrilamine, 20–30 Ci/mmol, from Dupont NEN Life Science Products, Boston, Mass.), chlorpheniramine maleate (from Schering-Plough Corporation, Kenilworth, N.J.) as standard, stored as frozen $10^{-5}$, $10^{-6}$, $10^{-7}$, $10^{-8}$ M solutions.
1. The compounds for assay were independently solubilized at 1 mg/ml DMSO by vortexing, or if necessary by sonication. The first dilution, 100-fold, was made in 50 mM Tris-HCl, pH 7.5, at room temperature. The three or four subsequent ten-fold serial dilutions were made in 1% DMSO/50 mM Tris-HCl, pH 7.5. Drug solutions and assay plates were kept at room temperature during the course of the assay set up.
2. Test compounds were assayed at four or five concentrations: 1, 0.1, 0.01, 0.001, and 0.0001 μg/ml. Twenty μl of drug solution was pipeted into each of three wells. A chlorpheniramine maleate standard was assayed at $10^{-9}$ to $10^{-6}$ M, 20 µl of each of the appropriate solutions being pipeted into triplicate wells. Total and nonspecific ($10^{-6}$M chlorpheniramine maleate) binding were determined at least in quadruplicate. For total binding, 20 µl of buffer was pipeted and for nonspecific 20 µl of $10^{-5}$M chlorpheniramine maleate was pipeted into each well.

3. [$^3$H]Pyrilamine was diluted approximately 2000-fold with ice-cold mM Tris-HCl, pH 7.5 (to a working concentration of 20–25 nM), and put on ice.

4. A frozen tissue pellet was thawed in a 25° C. water bath, resuspended in 50 mM Tris-HCl, pH 7.5, at 1.7–2 mg/ml by brief break-up on the Polytron, and put on ice.

5. Twenty µl of diluted [$^3$H]pyrilamine was added to each well.

6. One hundred fifty µl of tissue suspension was added to each well.

7. The top of the plate was covered and it was placed in a 25° C. shaking water bath (about 60 oscillations/min) for 30 min.

8. Samples were filtered on a Tomtec Mach 2 harvester (available from Tomtec Corporation, Orange, Conn.) through a GF/B filter mat (from Wallac, Inc., Gaithersburg, Md.) presoaked in 0.3% polyethylenimine. Each sample was thrice washed with ice-cold 50 mM Tris-HCl, pH 7.5 dried 20 sec on the Tomtec, and dried 3–4 min in a microwave oven on a paper towel. The filter was impregnated with MELTILEX brand wax scintillant (from Wallac Corporation) and counted on a Betaplate scintillation counter (from Wallac Corporation).

9. Specific binding was determined as the difference between total and nonspecific binding. The percent inhibition in the presence of inhibitor or standard was determined using the formula:

[1-(sample binding-nonspecific binding)/specific binding]×100

For compounds that inhibit more than 50% at 1 µg/ml, an $IC_{50}$ value was interpolated from proximate concentrations. The value was converted to a nM value using the compound formula weight and a $K_i$ value was calculated using the equation of Cheng and Prusoff ($K_1$=$IC_{50}$/(1+[L]/$K_D$), [Y-C. Cheng and W. H. Prusoff, "Relationship between the inhibitory constant ($K_i$) and the concentration of inhibitor which causes 50 percent inhibition ($IC_{50}$) of an enzymatic reaction", *Biochem. Pharmacol.* 22 (1973) 3099–3108]. Lower value of $K_i$ indicates greater binding affinity.

General Procedure for $H_3$-Receptor Binding Assay

The source of the $H_3$ receptors in this experiment was guinea pig brain. The animals weighed 400–600 g. The brain tissue was homogenized with a solution of 50 mM Tris, pH 7.5. The final concentration of tissue in the homogenization buffer was 10% w/v. The homogenates were centrifuged at 1,000×g for 10 min. in order to remove clumps of tissue and debris. The resulting supernatants were then centrifuged at 50,000×g for 20 min. in order to sediment the membranes, which were next washed three times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 µg/ml with 0.1% DMSO. Membranes were then added (400 µg of protein) to the reaction tubes. The reaction was started by the addition of 3 nM [$^3$H]R-α-methyl histamine (8.8 Ci/mmol) or 3 nM [$^3$H]N$^α$-methyl histamine (80 Ci/mmol) and continued under incubation at 30° C. for 30 min. Bound ligand was separated from unbound ligand by filtration, and the amount of radioactive ligand bound to the membranes was quantitated by liquid scintillation spectrometry. All incubations were performed in duplicate and the standard error was always less than 10%. Compounds that inhibited more than 70% of the specific binding of radioactive ligand to the receptor were serially diluted to determine a $K_i$ (nM). The results are given in Table 1 for the HCl salt of the indicated compounds.

TABLE 1

| STRUCTURE | $H_3$ Ki (nM) | $H_3$ % inhibition | $H_1$ Ki (nM) | $H_1$ % inhibition |
|---|---|---|---|---|
| 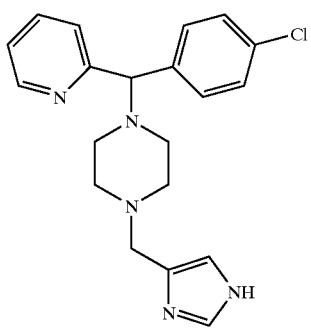 | 73 | | 5 | |

TABLE 1-continued

| STRUCTURE | H₃ Ki (nM) | H₃ % inhibition | H₁ Ki (nM) | H₁ % inhibition |
| --- | --- | --- | --- | --- |
| 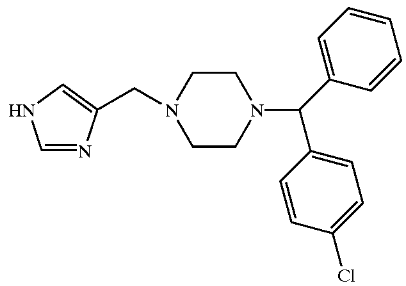 | 101 | | 1.7 | |
| | | 15 | | |
| | 62 | | 80 | |
| 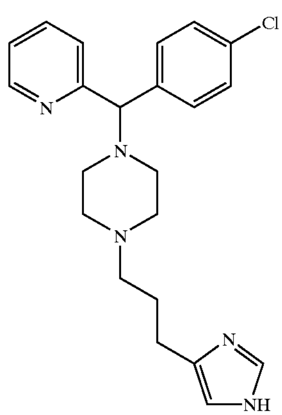 | 66 | | 40 | |

TABLE 1-continued
| STRUCTURE | H₃ Ki (nM) | H₃ % inhibition | H₁ Ki (nM) | H₁ % inhibition |
|---|---|---|---|---|
| 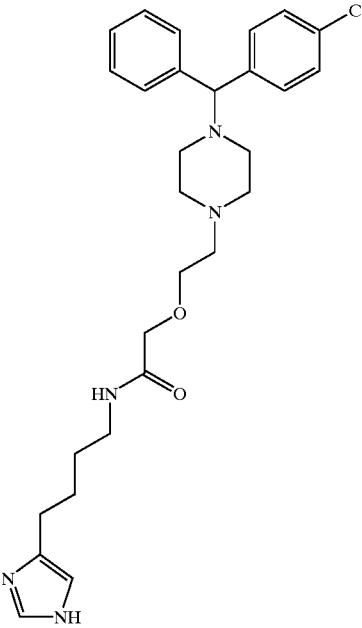 | 39 | | 11 | |
| 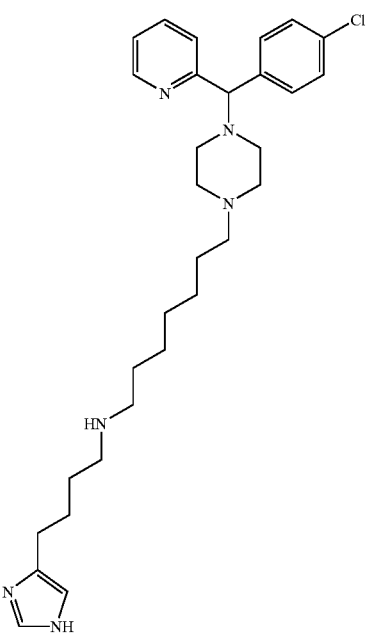 | 21 | | 18.5 | |

TABLE 1-continued
| STRUCTURE | H₃ Ki (nM) | H₃ % inhibition | H₁ Ki (nM) | H₁ % inhibition |
|---|---|---|---|---|
| 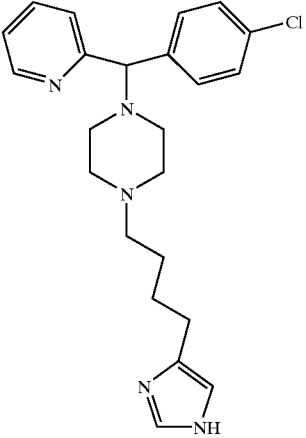 | 39 | | 5 | |
| 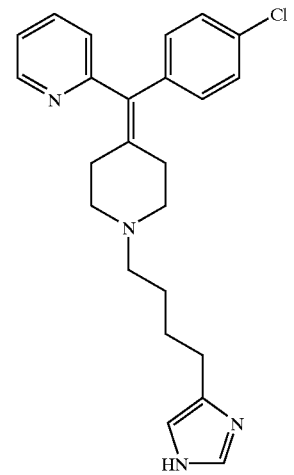 | 3 | | 4.5 | |
| 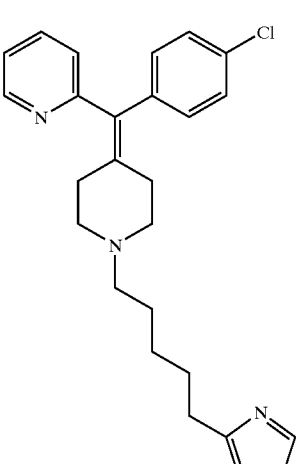 | 8 | | 4.5 | |

TABLE 1-continued
| STRUCTURE | H₃ Ki (nM) | H₃ % inhibition | H₁ Ki (nM) | H₁ % inhibition |
|---|---|---|---|---|
| 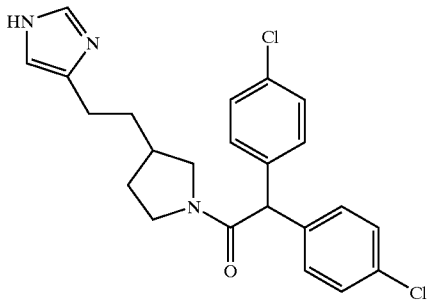 | 9.5 | | | 2 |
| 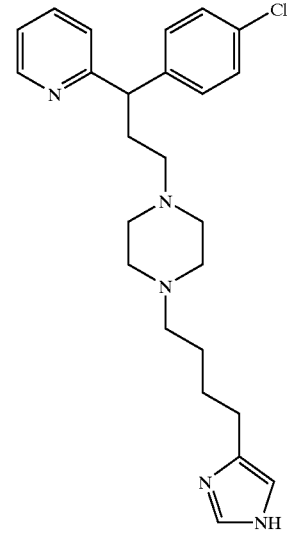 | 7 | | 21 | |
| 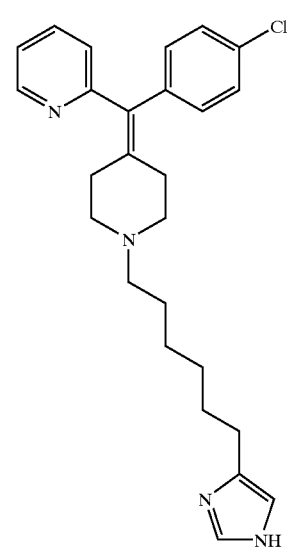 | 11 | | 3 | |

TABLE 1-continued
| STRUCTURE | H₃ Ki (nM) | H₃ % inhibition | H₁ Ki (nM) | H₁ % inhibition |
|---|---|---|---|---|
| 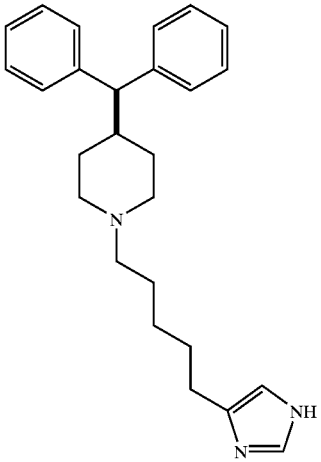 | 19 | | 28 | |
| 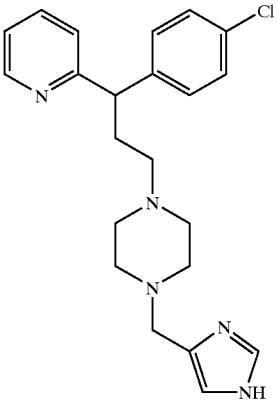 | 130 | | 25 | |
| 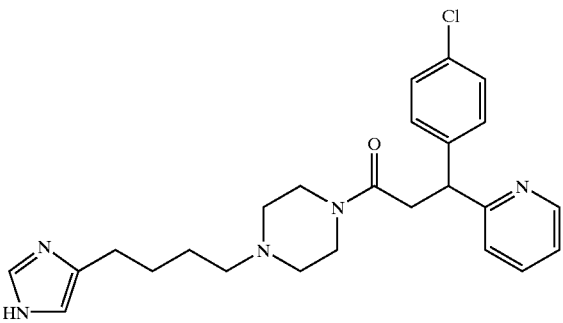 | 32 | | 14 | |
| 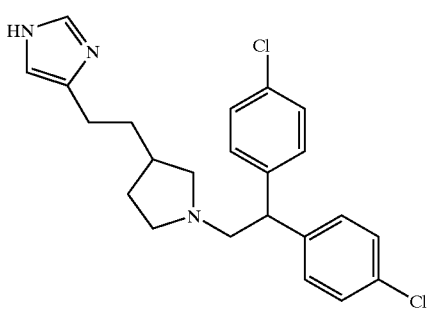 | 25 | | 18 | |

TABLE 1-continued

| STRUCTURE | H$_3$ Ki (nM) | H$_3$ % inhibition | H$_1$ Ki (nM) | H$_1$ % inhibition |
|---|---|---|---|---|
| 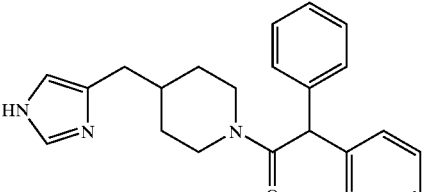 | | 66 | | 50 |
| 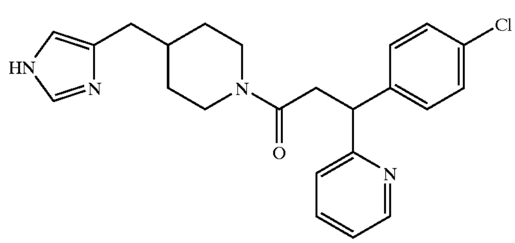 | 0.3 | | 19 | |

From these test results and the background knowledge about the compounds described in the references in the section "Background of the Invention", it would be apparent to the skilled artisan that the compounds of the invention have utility in treating inflammation, allergy, diseases of the GI-tract, cardiovascular disease, disturbances of the central nervous system and the like diseases stated earlier.

What is claimed is:

1. A compound exhibiting H$_3$ antagonist activity, or enantiomers, stereoisomers and tautomers of said compound, or pharmaceutically acceptable salts or solvates of said compound, said compound being selected from the compounds with structures listed below:

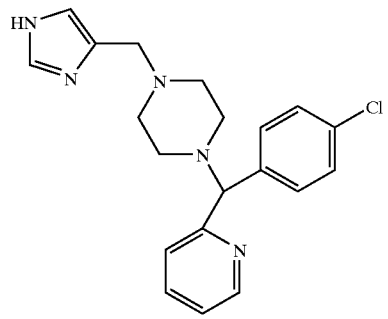

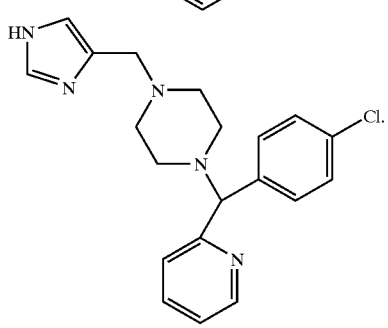

2. A compound exhibiting both H$_1$ and H$_3$ antagonist activity, or enantiomers, stereoisomers and tautomers of said compound, or pharmaceutically acceptable salts or solvates of said compound, said compound being selected from the compounds with structures listed below:

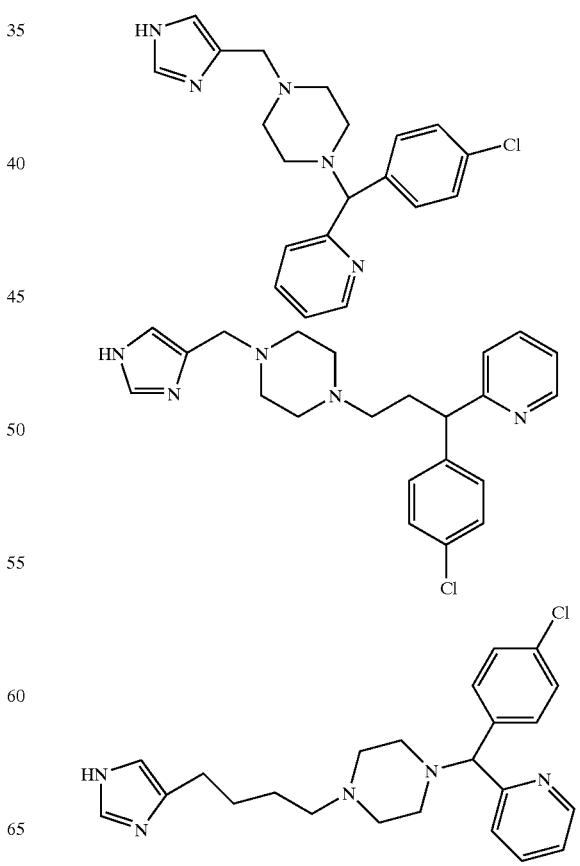

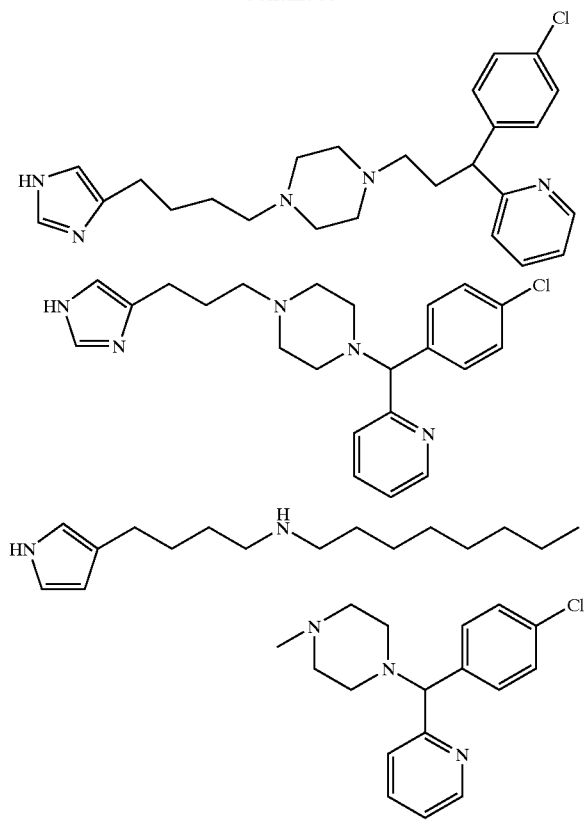

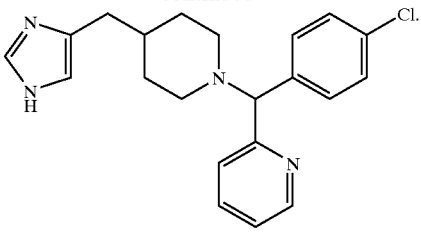

3. A pharmaceutical composition for treating gastrointestinal disorders, said composition comprising therapeutically effective amount of a compound of claim 1 or claim 2 and a pharmaceutically acceptable carrier.

4. A method of preparing a pharmaceutical composition for treating gastrointestinal disorders, said method comprising bringing into intimate contact a compound of claim 1 and a pharmaceutically acceptable carrier.

5. A method of preparing a pharmaceutical composition for treating gastrointestinal disorders, said method comprising bringing into intimate contact a compound of claim 2 and a pharmaceutically acceptable carrier.

6. A method of treating gastrointestinal disorders, said method comprising administering to a mammalian patient in need of such treatment a pharmaceutical composition which comprises therapeutically effective amounts of a compound of claim 1.

7. A method of treating gastrointestinal disorders, said method comprising administering to a mammalian patient in need of such treatment a pharmaceutical composition which comprises therapeutically effective amounts of a compound of claim 2.

* * * * *

UNITED STATES PATENT AND TRADEMARK OFFICE
CERTIFICATE OF CORRECTION

PATENT NO. : 6,762,186 B2  Page 1 of 1
DATED : July 13, 2004
INVENTOR(S) : Shih et al.

It is certified that error appears in the above-identified patent and that said Letters Patent is hereby corrected as shown below:

<u>Title page,</u>
Item [75], Inventors, should read:
-- Neng-Yang shih, North Caldwell, NJ (US;
Robert G. Aslanian, Rockaway, NJ (US);
Daniel M. Solomon, Edison, NJ (US);
Suart B. Rosenblum, West Orange, NJ (US);
Mwangi Wa Mutahi, Edison, NJ (US);
Wing C. Tom, Cedar Grove, NJ (US);
Kevin D. McCormick, Edison, NJ (US);
John J. Piwinski, Clinton Township, NJ (US);
Ronald Wolin, San Diego, CA (US) --.

Signed and Sealed this

Thirtieth Day of November, 2004

JON W. DUDAS
*Director of the United States Patent and Trademark Office*